United States Patent
Wolber

(10) Patent No.: US 6,284,465 B1
(45) Date of Patent: Sep. 4, 2001

(54) APPARATUS, SYSTEMS AND METHOD FOR LOCATING NUCLEIC ACIDS BOUND TO SURFACES

(75) Inventor: Paul K. Wolber, Los Altos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/292,289

(22) Filed: Apr. 15, 1999

(51) Int. Cl.7 .............................. C12Q 1/68; G01N 21/29
(52) U.S. Cl. ........................ 435/6; 436/94; 250/559.29; 422/82.05
(58) Field of Search .......................... 435/6; 250/559.29; 422/82.05; 436/94

(56) References Cited

U.S. PATENT DOCUMENTS

| | | | |
|---|---|---|---|
| 5,508,178 | 4/1996 | Rose et al. | 435/91.1 |
| 5,578,832 | 11/1996 | Trulson et al. | 250/458.1 |
| 5,585,639 | 12/1996 | Dorsel et al. | 250/458.1 |
| 5,721,435 | 2/1998 | Troll | 250/559.29 |
| 5,760,951 | 6/1998 | Dixon et al. | 359/385 |
| 5,763,870 | 6/1998 | Sadler et al. | 250/201.2 |
| 5,800,992 * | 9/1998 | Fodor et al. | 435/6 |
| 5,856,174 | 1/1999 | Lipshutz et al. | 435/286.5 |
| 6,045,996 * | 4/2000 | Cronin et al. | 435/6 |

FOREIGN PATENT DOCUMENTS

WO 00/34523   6/2000   (WO) .

* cited by examiner

Primary Examiner—Kenneth R. Horlick

(57) ABSTRACT

An apparatus, systems and method for locating nucleic acids in an array on a substrate have self-locating nucleic acid features. The nucleic acid features produce nucleotide-dependent location signals or optically detectable contrast between nucleotide-bound regions and non-nucleotide-bound regions of the substrate when scanned by an optical scanner. When used as analytical tools for monitoring gene expression and mutations in gene sequences, the nucleotide features are hybridized with nucleic acids of known or unknown sequences. The apparatus, systems and method locate both weakly and strongly hybridized nucleotide features on the substrate for identification of target nucleic acid sequences. The nucleotide feature signals or contrast are independent of the optical signals conventionally produced by the hybridized nucleotides. Therefore, the apparatus, systems and method locate all of the nucleotide features, hybridized or not, independently of the extent of hybridization. The present invention advantageously self-locates both bright and dim hybridized features on an array substrate and is therefore, independent of the random and systematic errors associated with the manufacturing equipment and processes. Moreover, the present invention provides a powerful quality control tool to the in situ synthesis process. The present invention provides information about what part or percentage of each feature contains full-length probes. The present optical scanning system detects optical signals from the nucleotide features independently of the signals from the hybridized nucleotides using essentially conventional scanning technology. The independently detected signals are processed such that all features are located and the hybridized features are accurately detected and analyzed.

34 Claims, 7 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA version of viral RNA
            sequence, bases 7-31"

(iii) HYPOTHETICAL: NO (iv) ANTI-SENSE: NO (vi) ORIGINAL SOURCE:
        (A) ORGANISM: Hepatitis C virus (ix) FEATURE:
        (A) NAME/KEY: modified_base
        (B) LOCATION: 1
        (C) IDENTIFICATION METHOD: experimental
        (D) OTHER INFORMATION: /evidence= EXPERIMENTAL
            /frequency= 0.9999
            /mod_base= OTHER
            /label= Cy3
            /note= "Cy3 fluorophore linked to 5' -OH via
            phosphodiester linkage"

(x) PUBLICATION INFORMATION:
        (A) AUTHORS: Trowbridge, R.
            Gowans, E. J.
        (B) TITLE: Molecular cloning of an Australian isolate of
            hepatitis C virus
        (C) JOURNAL: Arch. Virol.
        (D) VOLUME: 143
        (E) ISSUE: 3
        (F) PAGES: 501-511
        (G) DATE: 1998
        (K) RELEVANT RESIDUES IN SEQ ID NO:1: FROM 7 TO 31

(xi) SEQUENCE DESCRIPTION: SEQ ID NO:1:

actccaccat agatcactcc cctgt                                              25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(iii) HYPOTHETICAL: NO (iv) ANTI-SENSE: NO (ix) FEATURE:
        (A) NAME/KEY: modified_base
        (B) LOCATION: 1
        (C) IDENTIFICATION METHOD: experimental
        (D) OTHER INFORMATION: /evidence= EXPERIMENTAL
            /frequency= 0.9999
            /mod_base= OTHER
            /label= Cy5
            /note= "Cy5 fluorophore linked to 5'-OH via -continued phosphodiester linkage"

(xi) SEQUENCE DESCRIPTION: SEQ ID NO:2:

ggatacactg accagctacg atgat                                            25

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA version of viral RNA
            sequence, bases 7-31"

(iii) HYPOTHETICAL: NO (iv) ANTI-SENSE: NO (vi) ORIGINAL SOURCE:
        (A) ORGANISM: Hepatitis C virus (ix) FEATURE:
        (A) NAME/KEY: modified_base
        (B) LOCATION: 25
        (C) IDENTIFICATION METHOD: experimental
        (D) OTHER INFORMATION: /evidence= EXPERIMENTAL
            /frequency= 0.9999
            /mod_base= OTHER
            /label= biotin
            /note= "Biotin label linked to 3' -OH via phosphodiester
            linkage"

(x) PUBLICATION INFORMATION:
        (A) AUTHORS: Trowbridge, R.
            Gowans, E. J.
        (B) TITLE: Molecular cloning of an Australian isolate of
            hepatitis C virus
        (C) JOURNAL: Arch. Virol.
        (D) VOLUME: 143
        (E) ISSUE: 3
        (F) PAGES: 501-511
        (G) DATE: 1998
        (K) RELEVANT RESIDUES IN SEQ ID NO:1: FROM 7 TO 31

(xi) SEQUENCE DESCRIPTION: SEQ ID NO:3:

actccaccat agatcactcc cctgt                                            25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic"

(iii) HYPOTHETICAL: NO (iv) ANTI-SENSE: NO (ix) FEATURE:
        (A) NAME/KEY: modified_base
        (B) LOCATION: 25
        (C) IDENTIFICATION METHOD: experimental
        (D) OTHER INFORMATION: /evidence= EXPERIMENTAL
            /frequency= 0.9999
            /mod_base= OTHER
            /label= biotin
            /note= "Biotin label linked to 3'-OH via phosphodiester
            linkage"

-continued (xi) SEQUENCE DESCRIPTION: SEQ ID NO:4:

ggatacactg accagctacg atgat                                    25

(2) INFORMATION FOR SEQ ID NO:5:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA version of viral RNA
           sequence, bases 7-31"

(iii) HYPOTHETICAL: NO (iv) ANTI-SENSE: NO (vi) ORIGINAL SOURCE:
       (A) ORGANISM: Hepatitis C virus (ix) FEATURE:
       (A) NAME/KEY: modified_base
       (B) LOCATION: 1
       (C) IDENTIFICATION METHOD: experimental
       (D) OTHER INFORMATION: /evidence= EXPERIMENTAL
           /frequency= 0.9999
           /mod_base= OTHER
           /label= Cy5
           /note= "Cy5 fluorophore linked to 5' -OH via
           phosphodiester linkage"

(x) PUBLICATION INFORMATION:
       (A) AUTHORS: Trowbridge, R.
           Gowans, E. J.
       (B) TITLE: Molecular cloning of an Australian isolate of
           hepatitis C virus
       (C) JOURNAL: Arch. Virol.
       (D) VOLUME: 143
       (E) ISSUE: 3
       (F) PAGES: 501-511
       (G) DATE: 1998
       (K) RELEVANT RESIDUES IN SEQ ID NO:1: FROM 7 TO 31

(xi) SEQUENCE DESCRIPTION: SEQ ID NO:5:

actccaccat agatcactcc cctgt                                    25

APPARATUS, SYSTEMS AND METHOD FOR LOCATING NUCLEIC ACIDS BOUND TO SURFACES

TECHNICAL FIELD

This invention relates to analytical tools and methods for monitoring levels of gene expression and mutations in gene sequences. In particular, the invention relates to an apparatus, system and method of locating hybridized nucleic acid features on a substrate.

BACKGROUND ART

Immobilized oligonucleotides or polynucleotides of known nucleic acid sequences in an array on a substrate can be used as "probes" for monitoring levels of gene expression or to determine the absence or presence of known or new mutations in gene sequences. Sequences of nucleic acids are synthesized into polynucleotides and oligonucleotides either directly on the substrate (in situ), or indirectly (e.g., pre-synthesized) and deposited onto the substrate into an array pattern using well-known methods. Such methods are referenced below. These oligonucleotides are immobilized on the substrate in the array pattern.

The plurality of probes in each location in the array is known in the art as a "nucleic acid feature" or "feature". A feature is defined as a locus onto which a large number of probes, all having the same nucleotide sequence are immobilized. The oligonucleotide probes are exposed, for hybridization purposes, to a sample containing nucleic acids of known sequences at unknown concentrations, or unknown sequences, to be tested or evaluated. These nucleic acids are known in the art as "targets". Note that some investigators also use the reverse definition, referring to the surface-bound oligonucleotides as targets and the solution sample nucleic acids as probes. Henceforth, this application shall use "probes" to describe surface-bound oligonucleotides and "targets" to describe nucleic acids in solution that comprise the analytic sample in some assay or procedure. The nucleic acids or nucleotides in the target sample may be complementary to the nucleic acid or nucleotide sequences in the oligonucleotide probes.

Hybridization is the process where complementary nucleic acids will pair up, associate or bond together. Using well-known processes and conditions for hybridization, the sample nucleic acid "targets", will hybridize with the nucleic acids of known oligonucleotide probe sequences and thus, information about the target samples can be obtained. The processes and conditions of hybridization between nucleotide sequences are referenced below.

Depending on the make-up of the target sample, hybridization of probe features may or may not occur at all probe feature locations and will occur to varying degrees at the different probe feature locations. After hybridization of the targets with the probe features, the array is analyzed by well-known methods. Hybridized arrays are often interrogated using optical methods. Typically, the targets are labeled using well known methods and with well-known substances, e.g. a fluorophore that will fluoresce when exposed to a light source. The targets are labeled with a fluorophore either before the targets are applied to the array substrate, or labeled with a fluorophore after hybridization with an array substrate, such that the fluorophore will associate only with probe-bound hybridized targets.

Typically, measuring the hybridization to an array of known nucleic acid probes gives valuable information about the target samples. A focused light source (usually a laser) is scanned across the hybridized array causing the hybridized areas to emit an optical signal, such as fluorescence. The fluorophore-specific fluorescence data is collected and measured during the scanning operation, and then an image of the array is reconstructed via appropriate algorithms, software and computer hardware. The expected or intended locations of probe nucleic acid features can then be combined with the fluorescence intensities measured at those locations, to yield the data that is then used to determine gene expression levels or nucleic acid sequence of the target samples. The process of collecting data from expected probe locations is referred to as "feature extraction". The conventional equipment and methods of feature extraction are limited by their dependence upon the expected or intended location of the probe features on the substrate array, which is subject to the accuracy of the manufacturing equipment.

The scanning equipment typically used for the evaluation of hybridized arrays includes a scanning fluorometer and is commercially available from different sources, such as Molecular Dynamics of Sunnyvale, Calif., General Scanning of Watertown, Mass., Hewlett Packard of Palo Alto, Calif., or Hitachi USA of So. San Francisco, Calif. Analysis of the data, (i.e., collection, reconstruction of image, comparison and interpretation of data) is performed with associated computer systems and commercially available software, such as IMAGEQUANT™ by Molecular Dynamics or GENECHIP™ by Affymetrix of Santa Clara, Calif.

The laser light source generates a collimated beam. The collimated beam sequentially illuminates small surface regions of known location. The resulting fluorescence signals from the surface regions are collected either confocally (employing the same lens used to focus the laser light onto the array) or off-axis (using a separate lens positioned to one side of the lens used to focus the laser onto the array). The collected signals are transmitted through appropriate spectral filters, to an optical detector. A recording device, such as a computer memory, records the detected signals and builds up a raster scan file of intensities as a function of position, or time as it relates to the position. Such intensities, as a function of position, shall henceforth be referred to as "pixels". The pixels within a region centered upon the expected or intended position of a feature can be averaged to yield the relative quantity of target hybridized to the probe in that feature, if the expected or intended position of the feature is sufficiently close to its true position. For a discussion of the optical scanning equipment, see for example, U.S. Pat. No. 5,760,951 (confocal scanner) and U.S. Pat. No. 5,585,639 (off axis scanner), each incorporated herein by reference.

A general problem in the feature extraction process described above is the extraction of features having weak or low fluorescence intensities, called "dim features". A feature that yields little or no hybridization to the target sample will produce a low average fluorescence intensity when scanned (i.e. will display poor intensity contrast, relative to a background). However the dim features are just as important in the analysis of genes as are bright features (having extensive hybridization). The majority of genes in a given cell type are expressed at low levels (for example, less than about 50 copies of the gene per cell). Therefore, an array constructed from features that measure expression levels of any plurality of available genes will result in a majority of the hybridized features being dim rather than bright.

If the dim hybridized probe feature is located or positioned accurately in the array and is of known shape, then accurate feature extraction can be performed automatically, using relatively simple algorithms. The computer is programmed to analyze predefined regions of interest on the array based on the expected or intended locations of the probe features that were placed by the manufacturing equipment. The computer will analyze the results of the optical scan by considering the predefined regions of interest. If a pixel within the raster-scan image of a dim feature is within the region of interest, the computer will include the pixel in its data collection.

One problem arises when the probe feature that produces a weak signal after hybridization is not accurately located on the array substrate by the manufacturing process. Although, it is conventional practice to provide fiduciary markings on the array substrate, for example, to which the manufacturing equipment aligns each manufacturing step, errors in the location of the features still occur. The fiduciary markings are also used during feature extraction. The optical scanning equipment aligns the light source with the array fiduciary markings and the computer aligns its predefined region for detection and analysis with the fiduciary markings on the substrate surface. When a pixel within the raster-scan image of a dim feature is outside the region of interest (i.e. the probe feature is misplaced or mislocated due to the manufacturing process, for example), the computer will not count the pixel. The computer will sum the intensities from all pixels within the region of interest, average the signals by dividing the sum by the total number of pixels involved and report the average signal per pixel within the region of interest. When the computer does not include pixels from the misplaced hybridized feature in the sum and extracts from an area on the substrate with no features or with partial features inaccurate data will result.

Another problem arises when the probe feature that produces a weak signal after hybridization is misshaped for some reason and the computer cannot detect the irregular shape. The computer will extract information from predefined regions with shapes that are capable of only partially overlapping the actual feature. The common source of misshapened features is in the manufacturing process. Common misshapened feature morphologies are annular features and football-shaped features. An annular feature has an intensity profile that looks like a donut rather than a uniform spot. Effectively, there are more nucleic acid probes at the edges than in the center of the feature. A football-shaped feature has an intensity profile shaped like the intersection of two or more overlapping circles. Effectively, there are more oligonucleotide probes on one side of the feature. Other, more complex morphologies such as crescents and defects due to scratches on the substrate surface are also observed. The computer is typically programmed to sample a disk-shaped region inside the edges of the feature, because a uniform spot is expected. When either an annular or football-shaped feature is sampled inside the edges, a quantity of potentially valuable information is overlooked, and a quantity of substandard information is included. Both measurement defects result in inaccurate assessment of the degree of hybridization of target to the probe feature.

When in situ synthesis of a 25-nucleotide probe feature is considered, the misshapened feature results from a given feature not being placed once, but instead 25 times, because probe ingredients are spotted onto each feature location 25 times. This process generates a Venn diagram of all of the spots (of all of the ingredients). If the spots are deposited in roughly the same place, the feature is approximately circular. Otherwise, if one or more spots are mispositioned during the synthesis, one could obtain a football-shaped feature, for example. Unless the equipment is preprogrammed to employ an alternative algorithm for extraction of misshapened and mislocated features, the quality of the resulting data suffers. However, all current algorithms fail to properly extract dim features that are misshaped or mispositioned.

The primary difficulty lies in the ability to determine with a level of certainty the actual position of the probe feature that gives rise to the weak signal to ensure its detection by the optical scanning equipment. A dim feature that is not located on the substrate consistently within the array pattern, may be missed during the feature extraction process, if the analysis equipment or the operator does not know the likely locations of inconsistently placed features. Therefore, this limitation in the conventional equipment and method yields less accurate results when analyzing the fluorescence data for the composition of the target sample.

The deposition of probes, or in situ synthesis thereof, on substrates is performed with automated equipment, as described above. Current manufacturing equipment can produce probe features ranging in size from about 20 to 1000 microns in diameter, with preferred size being equal to 200 microns in diameter or less. The features are positioned on substrates in arrays having a spacing less than or equal to two feature diameters, and preferably about 1.5 to 2 feature diameters center to center spacing. For example, if the probe features had an average diameter of 100 microns, the preferred center-to-center distance would be 150–200 microns. However, it is the goal in the industry to make the arrays smaller and more compact, since smaller arrays require less sample (which is usually in short supply), can be scanned more rapidly and are less expensive to manufacture. In addition, as features become smaller and more densely packed, more genes can be analyzed using an array of a given size; this again saves sample and reduces costs. Achieving smaller and more compact arrays will depend heavily on the manufacturing equipment and processing. It should be appreciated that as probe arrays for gene analysis become more density packed, very small errors in probe placement more severely impact the accuracy of the analysis of the hybridization results.

Any real manufacturing process is subject to both random and systematic errors in the dimensions of the manufactured artifact. The manufacturing processes used in creating arrays of nucleic acids features for gene analysis are no exception and therefore, nucleic acid feature locations are subject to both random and systematic errors. An error in the location of the feature on the array of greater than or equal to ten percent of the diameter could affect the scanned fluorescence data and produce inaccurate results by the conventional equipment and method. Since the regions of interest for probe analysis are predefined to typically exclude the edges of a feature, a location error of less than 10 percent of the diameter of the typically shaped feature, should not jeopardize the integrity of the collected data.

However, another manufacturing error that may result includes variations in the diameter of the probe feature. Variations in the diameter of a feature may result from surface chemistry problems on the surface of the substrate, such as changes in hydrophobicity of the surface. A higher than expected surface hydrophobicity will results in the feature having a smaller footprint, since the feature tends to bead up more on the more hydrophobic substrate surface. Therefore, the feature might be located in the correct place, but be only one half to three quarters of the diameter than was expected (i.e. the error is greater than 10 percent of the diameter). When the computer samples the predefined region of interest, it collects non-probe feature data in addition to the feature signal. The feature signal is degraded by the additional data.

When an array is subjected to hybridization with a target sample, either the hybridized feature will produce a bright fluorescence intensity (i.e. will display good intensity contrast, relative to a background) or a dim fluorescence intensity (i.e. will display poor intensity contrast, relative to the background) when scanned, typically due to the amount of hybridization that occurred with the target sample. If a poorly positioned or located hybridized feature is bright, it becomes self-locating. As long as the intended feature (and only the intended feature) overlaps a region of uncertainty drawn around the intended feature location, then any algorithm capable of recognizing a connected region of pixels whose intensities exceed some threshold can be used to find the actual feature, calculate its center and move the center of the data extraction region to coincide with the feature center. Such algorithms are well known to the art of image processing. A commercial implementation of such an algorithm can be found in the computer program IMAGEQUANT™ marketed by Molecular Dynamics (Sunnyvale, Calif.).

Unfortunately, dim features are not self-locating and therefore, the location of probe features that are inaccurately placed on a substrate must be determined in order to obtain accurate data during feature extraction of dim features. The problem of locating inaccurately placed probe features that result in weak signals after hybridization becomes particularly difficult as feature size decreases, because the relative importance of location errors increases at the same time that the total number of pixels in the digital array image that contain relevant data is decreasing. The physical laws governing the behavior of light limit the minimum size of a pixel in a raster-scan image obtained via laser-excited fluorescence. This minimum dimension ranges from about 3 microns (blue excitation light) to about 5 microns (red excitation light). Thus, a 100 micron diameter feature scanned by a red excitation laser is spread across approximately 310 pixels; a 50 micron diameter feature is spread across approximately 78 pixels, and a 25 micron diameter feature occupies only 19 pixels. For a 100 micron diameter feature, a 5 micron location error will subtract about 40 signal-containing pixels from the extraction process, and replace them with background pixels (approximately 13% error). The same 5 micron location error will introduce approximately 50% error into the extraction of a 25 micron diameter feature.

The conventional equipment and method of feature extraction rely on the locations of the probe features being those expected or intended from the manufacturing processes to analyze and identify the locations of hybridization. The uncertainty in the actual position of each feature in the array can compromise the detection of probe-bound hybridization targets, particularly when the hybridization signal density from a feature is weak ("dim feature").

For instance, if the conventional detection equipment is directed onto a spot that spans the margin of a dim feature and includes some substrate region, that has neither any probes nor hybridized targets bound onto it, then the total signal that reaches the detector from a spot fully within the feature boundary could yield a positive reading and the existence of the dim hybridized feature would be detected. It is common for the surface of the substrate to produce optical background noise (e.g. undesired signal) when the array is optically scanned to identify hybridized features. If the signal from the hybridized feature is weak, it may be difficult to distinguish the dim feature from the background noise. When the background signal noise from the surface of the substrate is stronger than the dim feature, the feature is described as a "negative feature". Most arrays contain at least a few negative features; these further add to the difficulty of locating dim features. In addition, "false negative" results are possible when the dim feature is mislocated on the substrate. A false negative reading is caused by missing a signal from a dim feature that was above the detection threshold because the equipment extracted mostly the substrate region or background and not the feature.

Therefore, either the array manufacturing process must be improved to the point that location and other manufacturing errors are negligible, or other methods must be used to locate dim features, or both.

Methods to generally locate features on a substrate are disclosed in U.S. Pat. No. 5,721,435, issued to Troll and assigned to the assignee of the present invention, and is incorporated herein by this reference. The methods of Troll include a plurality of reference markings and test spots on an array, all of which produce signals when optically scanned that are detected and evaluated to determine the location of the test spots. The reference markings have optically unique signatures to distinguish them from the signals from the test spots. The reference markings are spaced apart at known distances and serve to provide a constant calibration for the scanning equipment. The reference markings are typically laser-etched or metal-plated alignment marks that are written to the substrate surface. This method of feature location is commonly referred to as "dead-reckoning" from a mixture of design parameters and physical landmarks.

Another method to generally locate features that can be used to locate dim features is user-assisted feature extraction ("by hand"). Although these methods work well to generally locate features on a substrate, without further intervention, they are not much better at locating dim features that are mislocated (i.e., not properly placed) on the substrate by the manufacturing equipment. Dead reckoning is degraded by both uncompensated systematic location errors and random location errors. Finally, user-assisted extraction is, by definition, subjective and not automated; it is also slow, tedious and subject to errors caused by user fatigue.

Thus, it would be advantageous to have an apparatus, system and method to accurately locate probe features bound to a substrate regardless of whether the features produce a dim or bright fluorescence when hybridized with a target and regardless of the accuracy of the manufacturing equipment and processes, preferably utilizing the features of conventional scanning and analysis equipment.

SUMMARY OF THE INVENTION

The present invention provides an apparatus, systems and method utilizing self-locating nucleic acid probe features. By self-locating, it is meant that the location of the nucleic acid probe features will be evident when scanned by an optical scanner by producing probe-dependent location signals or from having optically-detectable contrast between probe-containing regions and non-probe-containing regions of the substrate. The self-locating probe features in accordance with the invention are independent of the signals generated from the hybridization by target samples and independent of whether the probe features were accurately positioned on the substrate during the manufacturing process. The present apparatus, systems and method advantageously self-locates both bright and dim hybridized features on an array substrate using conventional scanning technology, wherein the conventional scanning equipment is uniquely adapted to detect optical signals from the probe features independently of the fluorescence by the hybridized targets.

In accordance with the present invention, the actual location of all features are determined with the present optical scanning system which measures an additional signal that depends upon the presence of surface-bound or surface-containing nucleic acid probes, but is independent of the presence or absence of hybridized target nucleic acids. This is accomplished by either (1) extracting the probe feature signal off-axis to the original excitation beam or confocally to the excitation beam, or (2) collecting the probe feature signal through the fluorescence emission channel. When the signal from the surface bound probes is a scattered light signal, the present optical system advantageously masks reflected excitation beam so that it does not interfere with the scattered light detection. When the surface bound probe signal is fluorescence, the optical system of the invention advantageously separately detects different fluorescence characteristics than those from the hybridized target signal. Advantageously, the result is essentially a parallel elaboration of functions already present in the scanner: an additional optical signal is measured during the scan, and stored in the same manner as the fluorescence signal scan(s). Collection of the additional signal requires the installation of optical components similar to those used to collect the hybridization signal, and can make use of some components (e.g. lens for confocal excitation and signal collection) already present in the scanner.

The present apparatus and system for locating features comprise a substrate, a plurality of nucleic acid probes bound to a surface of the substrate and regions on the substrate surface that are devoid of the plurality of probes. The probes are capable of producing a signal when scanned with an optical scanner such that the optical signal indicates the actual location of each probe on the substrate. In one embodiment, the apparatus and system of the present invention further comprise a plurality of targets that are hybridized to at least some of the probes. Each target is capable of producing an optical signal different from the optical signal produced by the probes when scanned with the optical scanner. The probe optical signal indicates the actual location of each probe independently of the hybridization by the plurality of targets and independently of the accuracy of the manufacturing processes that assembled the present apparatus.

The present system for locating further comprises an optical scanning system for optically scanning the plurality of probes, such that each probe produces the optical signal. The present optical scanning system includes an optical stimulus or light source, a detection subsystem for detecting the signals and an analysis subsystem to analyze the optical signal thus produced and to locate each probe of the plurality of probes on the substrate. The detection subsystem distinguishes between the optical signals produced from the probes and the signals produced by the hybridized targets. The detection and analysis subsystems locate each probe of the plurality of probes on the substrate independently of optical signal from the hybridized targets. The location and subsequent identification of the targets are obtained from the actual location and identity of the probe features. The present system advantageously locates dim and bright hybridized features independently of the accuracy of the manufacturing process and of the extent of hybridization by target compounds.

The present method of locating a plurality of probes positions on a substrate includes providing a plurality of nucleic acid probes on a substrate in a pattern such that there are regions on the substrate that are devoid of the plurality of probes. The plurality of probes produces an optical signal when scanned optically. The optical signal is detected and analyzed and the location of each probe on the substrate is determined based on the detected optical signal from the bound probe features. In one embodiment, the method further includes hybridizing at least some of the plurality of probes with a plurality of targets. The targets are rendered to produce an optical signal different from the probe's optical signal when scanned optically. When the plurality of probes are optically scanned, the plurality of probes produces the probe optical signal and the plurality of hybridized targets produces the target's optical signal independently of the probe optical signal. These signals are detected and analyzed and the location of each probe on the substrate is determined based on the detected optical signal from the probe independently of the detected optical signal from the hybridized targets. The present method determines the location and subsequent identity of the hybridized targets from the actual locations and identity of the probe features.

In a preferred embodiment of the apparatus, systems and method, there is an optically-detectable contrast between the probe features and the regions on the substrate devoid of probes. This optically-detectable contrast produces an optical signal when optically stimulated by the scanning system to provide information about the actual locations of the probe features.

In accordance with the invention, the probe features can be made capable of producing an optical signal or to have sufficient optically-detectable contrast from the substrate in many different ways. In the preferred embodiments, either (i) at least one nucleotide in each oligonucleotide probe includes a signal producing system, or (ii) the non-probe-bound substrate regions are directly or indirectly labeled with an optically sensitive substance to produce optical contrast. Further, optical contrast or an optical signal associated with the probe locations can be obtained by making use of the optical properties inherent in the probe DNA. Moreover, the optical properties intrinsic to a characteristic that differs between probe-bound regions and non-probe-bound regions of the substrate can be used to generate sufficient optical contrast and signal for the purposes of the invention.

In accordance with the preferred embodiment of the present invention, if the manufacturing step that generates the probe optical signal is dependent upon the last step of the probe synthesis having gone correctly, e.g. attaching a member of a specific binding pair to the last nucleotide of the probe as the last step, then a probe optical signal will result only where fill length probes have been manufactured on the apparatus. This aspect of the preferred embodiment unexpectedly and advantageously adds quality control to present invention. Not only does the present invention comprise features that are self-locating, but also the present invention provides information about what part or percentage of the feature contains the full-length probes.

Preferably and advantageously, the presence of surface-bound nucleic acid probes is essentially constant within all full-length features on a substrate. This is because the signal producing system (used in a preferred embodiment) is quantitatively bound to probe polynucleotide on the surface, and is independent of the amount of target that is hybridized to the surface-bound probes. The signal generated by the labeled probe when optically scanned allows simple, objective detection of the region containing surface-bound probes.

The present invention requires that the probe features are discreet, i.e., there are regions on the substrate surface devoid of probe nucleic acid in between the probe features. This is so that the necessary contrast between features and the devoid regions is created and is optically detectable. The requirement for discreet probe features is met by most arrays manufactured by printing-based deposition or in situ synthesis techniques. Printing technologies are based upon applying chemical reactants to known locations on the array surface as discreet, localized droplets. The space between features prevents droplet merger and loss of reactant localization.

Moreover, manufacturing problems associated with variations in the size or shape of the probe feature are advantageously and unexpectedly overcome by the present invention, because the present invention provides spatial resolution so that the extent of the feature as well as its central location are determined.

BRIEF DESCRIPTION OF THE DRAWINGS

The various features and advantages of the present invention may be more readily understood with reference to the following detailed description and Examples taken in conjunction with the accompanying drawings, where like reference numerals designate like structural elements, and in which.

MODES FOR CARRYING OUT THE INVENTION

Definitions

Figure 1:
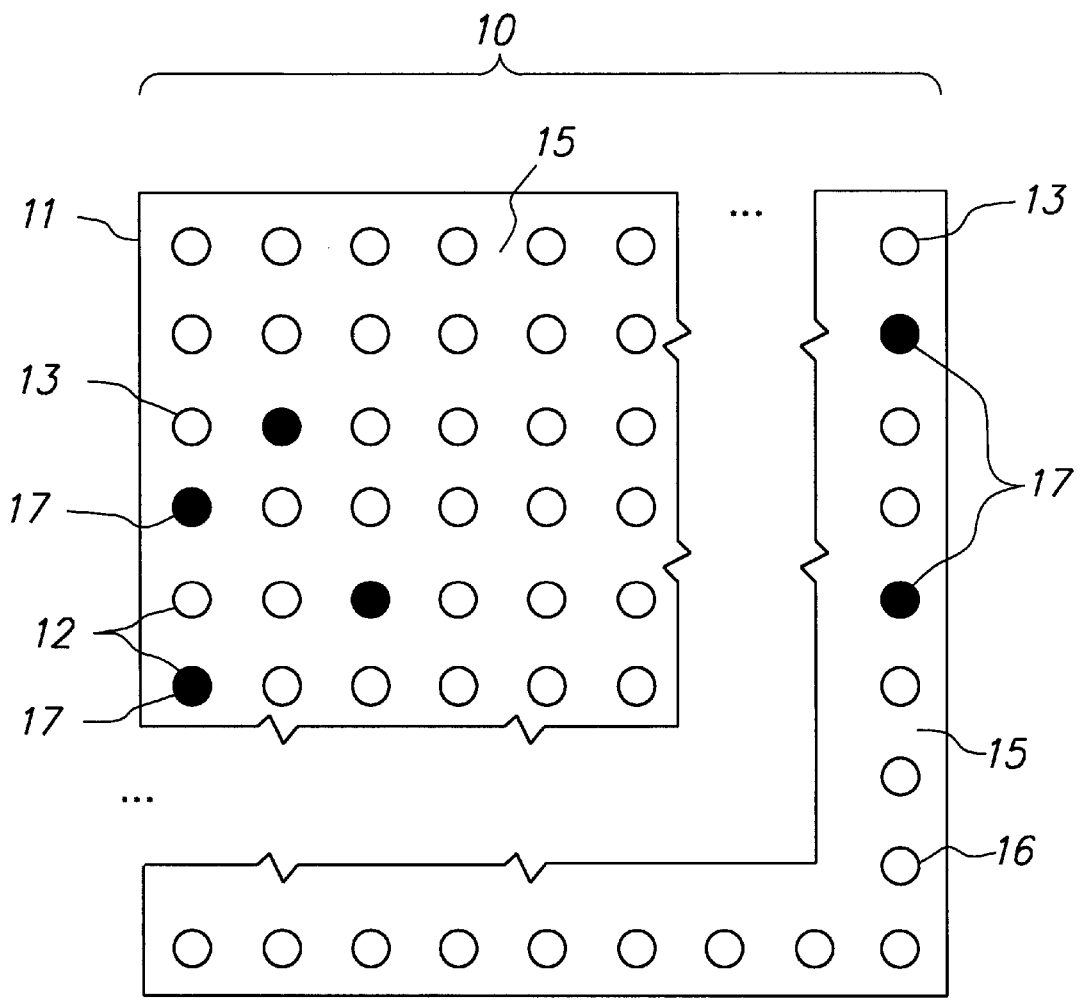
FIG. 1 illustrates a front view of an idealized array of nucleic acid probes in accordance with the present invention.

The following terms are intended to have the following general meanings as they are used herein:

Polynucleotide—a compound or composition that is a polymeric nucleotide or nucleic acid polymer. The polynucleotide may be a natural compound or a synthetic compound. In the context of an assay, the polynucleotide can have from about 5 to 5,000,000 or more nucleotides. The larger polynucleotides are generally found in the natural state. In an isolated state the polynucleotide can have a bout 30 to 50,000 or more nucleotides, usually about 100 to 20,000 nucleotides, more frequently 500 to 10,000 nucleotides. It is thus obvious that isolation of a polynucleotide from the natural state often results in fragmentation. The polynucleotides include nucleic acids, and fragments thereof, from any source in purified or unpurified form including DNA, double-stranded or single stranded (dsDNA and ssDNA), and RNA, including t-RNA, m-RNA, r-RNA, mitochondrial DNA and RNA, chloroplast DNA and RNA, DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, double stranded DNA (dsDNA) can be heated at 90–100° C. for a period of about 1 to 10 minutes to produce denatured material, while RNA produced via transcription from a dsDNA template is already single stranded.

Target nucleotide sequence—a sequence of nucleotides to be identified, usually existing within a portion or all of a polynucleotide, usually a polynucleotide analyte. The identity of the target nucleotide sequence generally is known to an extent sufficient to allow preparation of various probe sequences hybridizable with the target nucleotide sequence.

The target sequence usually contains from about 30 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, usually, 10 to 100 nucleotides, more usually, 20 to 50 nucleotides, preferably, 10 to 30 nucleotides, more preferably, 20 to 30 nucleotides, and desirably about 25 nucleotides in length.

Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described in J. Messing (1983) Methods Enzymol. 101:20–78.

Other methods of oligonucleotide synthesis include phosphotriester and phosphodiester methods (Narang, et al., (1979) Meth. Enzymol 68:90) and synthesis on a support (Beaucage, et al. (1981) Tetrahedron Letters 22:1859–1862) as well as phosphoramidate techniques (Caruthers, M. H., et al., "Methods in Enzymology," Vol. 154, pp. 287–314 (1988) and others described in "Synthesis and Applications of DNA and RNA," S. A. Narang, editor, Academic Press, New York, 1987, and the references contained therein. Sequential addition of nucleotide phosphoramidites to surface-linked hydroxyl groups is described by T. Brown and Dorcas J. S. Brown in *Oligonucleotides and Analogues A Practical Approach*, F. Eckstein, editor, Oxford University Press, Oxford, pp 1–24 (1991), and incorporated herein by reference. The chemical synthesis via a photolithographic method of spatially addressable arrays of oligonucleotides bound to glass surfaces is described by A. C. Pease, et al., Proc. Nat. Aca. Sci. USA (1994) 91:5022–5026. Deposition of presynthesized oligonucleotides may be accomplished by (1) covalent linkage of a chemically modified oligonucleotide (e.g. aliphatic 1° amine) to the substrate surface bearing an amine-reactive group (e.g. aromatic isothiocyanate) as described in Z. Guo, R. A. Guilfoyle, A. J. Thiel, R. Wang, L. M. Smith, *Nucleic Acids Res* 22, 5456–65 (1994), incorporated herein by reference, or (2) adsorption to a substrate surface coated with a positively charged polyelectrolyte (e.g. poly-L- lysine), followed by cross-linking to the surface chemically or photochemically (e.g. covalent stabilization via ultraviolet (UV) photocrosslinking), as described in M. Schena, D. Shalon, R. W. Davis, P. O. Brown, *Science*, 270, 467–70 (1995), incorporated herein by reference. Common deposition equipment used for forming arrays includes that described in M. Schena et al. (cited above), A. C. Pease et al., *Proc. Natl. Acad. Sci. USA*, 91, 5022–6 (1994) and A. P. Blanchard, R. J. Kaiser, L. E. Hood, *Biosensors & Bioelectronics* 11, 687–690 (1996), each incorporated herein by reference.

Oligonucleotide probe—an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Modified nucleotide—a unit in a nucleic acid polymer that contains a modified base, sugar or phosphate group. The modified nucleotide can be produced by a chemical modification of a nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and the like and also include phosphorothioate, phosphite, ring atom modified derivatives, and so forth.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. Hybridization processes and conditions are described in J. Sambrook, E. F. Fritsch, T. Maniatis, *Molecular Cloning: A Laboratory Manual*, Cold Spring Harbor Laboratory Press, Cold Spring Harbor, Ed. $2^{nd}$, 1989, vol. 1–3, incorporated herein by reference. Conditions for hybridization typically include (1) high ionic strength solution, (2) at a controlled temperature, and (3) in the presence of carrier DNA and detergents and divalent cation chelators, all of which are well known in the art.

Hybridization efficiency—the productivity of a hybridization reaction measured as either the absolute or relative yield of oligonucleotide probe/polynucleotide target duplex formed under a given set of conditions in a given amount of time.

Complementary—Two sequences are complementary when the sequence of one can bind to (has an affinity to bond or associate with) the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs.

Substrate or surface—a porous or non-porous water insoluble material. The surface can have any one of a number of shapes, such as strip, plate, disk, rod, particle, including bead, and the like. The substrate can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Common substrates used for the arrays of probes are surface-derivatized glass or silica, or polymer membrane surfaces, as described in Z. Guo et al. (cited above) and U. Maskos, E. M. Southern, *Nucleic Acids Res* 20, 1679–84 (1992) and E. M. Southern et al., *Nucleic Acids Res* 22, 1368–73 (1994), both incorporated herein by reference.

Immobilization of oligonucleotides on a substrate or surface may be accomplished by well-known techniques, commonly available in the literature. See, for example, A. C. Pease, et al., *Proc. Nat. Acad. Sci. USA,* 91:5022–5026 (1994).

Label—a member of a signal producing system. Usually the label is part of a target nucleotide sequence or an oligonucleotide probe, either being conjugated thereto or otherwise bound thereto or associated therewith. For the present invention, a label is part of the target sequence and may be part of the oligonucleotide probe. The label is capable of being detected directly or indirectly. Labels include (i) reporter molecules that can be detected directly by virtue of generating a signal, e.g., a fluorophore, (ii) specific binding pair members that may be detected indirectly by subsequent binding to a cognate that contains a reporter molecule, e.g., biotin-streptavidin, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used. For example, the nucleic acid base is modified to include biotin, which binds to streptavidin that has been previously covalently linked to a fluorophore. Direct labels are commercially available from several manufacturers, including Boehringer-Mannheim and Amersham-Pharmacia Biotech. Boehringer-Mannheim also sells biotinylated nucleotides, and Amersham-Pharmacia Biotech also sells streptavidin labeled with a variety of fluorophores.

The reporter molecule can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label can generate a detectable signal either alone or together with other members of the signal producing system. As mentioned above, a reporter molecule can be bound directly to a nucleotide sequence or can become bound thereto by being bound to an specific binding pair (sbp) member complementary to an sbp member that is bound to a nucleotide sequence. Examples of particular labels or reporter molecules and their detection can be found in U.S. Pat. No. 5,508,178, the relevant disclosure of which is incorporated herein by reference. When a reporter molecule is not conjugated to a nucleotide sequence, the reporter molecule may be bound to an sbp member complementary to an sbp member that is bound to or part of a nucleotide sequence.

Signal Producing System—the signal producing system may have one or more components, at least one component being the label. The signal producing system generates a signal that typically relates to the presence or amount of a target polynucleotide in a medium. For the present invention, a signal producing system may be incorporated on the oligonucleotide probes and relates to the presence of probes in a medium. The signal producing system includes all of the reagents required to produce a measurable signal. Other components of the signal producing system may be included in the developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Signal-producing systems that may be employed in the present invention are those described more fully in U.S. Pat. No. 5,508,178, the relevant disclosure of which is incorporated herein by reference.

Ancillary Materials—Various ancillary materials will frequently be employed in the method and assays utilizing oligonucleotide probes designed in accordance with the present invention. For example, buffers and salts will normally be present in an assay medium, as well as stabilizers for the assay medium and the assay components. Frequently, in addition to these additives, proteins may be included, such as albumins, organic solvents such as formamide, quaternary ammonium salts, polycations such as spermine, surfactants, particularly non-ionic surfactants, binding enhancers, e.g., polyalkylene glycols, or the like.

Member of a specific binding pair ("sbp member")—one of two different molecules, having an area on the surface or in a cavity that specifically binds to and is thereby defined as complementary with a particular spatial and polar organization of the other molecule. The members of the specific binding pair are referred to as cognates or as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

DETAILED DESCRIPTION OF THE INVENTION

FIG. 1 illustrates the apparatus 10 of the present invention. Apparatus 10 comprises a plurality of nucleic acid probes 12 that is immobilized on the surface of a support or an array substrate 11, preferably in an essentially ordered arrangement of distinct features 13. In the preferred embodiment, each feature 13 has a large number of probes 12, the probes 12 in a particular feature have the same nucleotide sequence, and the features 13 differ by the nucleotide sequence of their respective probes 12. The probes 12 are made up of oligonucleotides or polynucleotides (for example cDNAs) of preferably known sequence or character. The term cDNA is a term of art and means "complementary" DNA. The cDNAs are produced by reverse-transcription of messenger RNA, and contain the Watson Crick complement of the original messenger RNA sequence. Between the features 13 are regions 15 of substrate surface that are devoid of immobilized nucleic acid probes 12, which serves to separate the features 13 from one another, rendering the features 13 as discreet entities on the surface of the substrate 11.

According to the invention, the probes 12 are synthesized either in situ, using standard methods of sequential phosphoramidite addition, or are synthesized by a conventional chemosynthetic technique (e.g. phosphoramidite chemistry) or biosynthetic techniques (e.g. polymerase chain reaction "PCR"), printed onto the array surface, and covalently linked to that surface. See T. Brown et al., *Oligonucleotides and Analogues A Practical Approach* and see M. Schena, et al., *Science*, (both of which are cited above). The probe ingredients are printed or added to the feature locations 13 of the substrate 11 surface preferably using a modified thermal or piezoelectric inkjet-printing device. Presynthesized probes 12 or probe compositions are printed, using the preferred printing device, on any of the array substrates 11 mentioned previously, and preferably, are immobilized on the substrate using a poly-L-lysine coated substrate surface. For the purposes of the invention, the array of probes may be fabricated using conventional photolithography techniques as well. See, for example, A. C. Pease et al., *Proc. Natl. Acad. Sci. USA* (cited above).

In accordance with the invention, the probe features 13 on apparatus 10 have the capability of producing an optical signal 14 either directly, or indirectly via an optically detected contrast 16 between the probe-bound regions 13 and the substrate regions 15 that are devoid of probe features, when optically stimulated by optical scanning equipment. Examples are described below of several ways to render the probe features 13 capable of producing the optical signal 14 or contrast 16. The Examples provided can be summarized as being in three categories (i) modified nucleotides—using direct or indirect labeling of the probe oligonucleotides 12; or direct or indirect labeling of the non-probe-bound substrate regions 15; (ii) using the optical properties inherent in the probe 12 DNA; and (iii) using optical properties intrinsic to a characteristic that differs between probe-bound regions 13 and non-probe-bound regions 15 of the substrate 11. It should be noted that numerous other examples and potential categories for the examples are possible and it is not the intent of the inventors to be limited in scope to the summary of the Examples provided above or to the detailed description of the Examples provided below. As long as an optical contrast 16 between probe-bound regions 13 and non-probe bound regions 15 of apparatus 10 exists, and the optical contrast 16 either directly or indirectly produces a signal 14 when scanned optically, the requirements of the invention are satisfied.

The Examples below pertaining to the direct or indirect labeling of the probe features 13 that ultimately provide the contrast 16 optical signal 14 for locating features 13 are preferred. Direct or indirect labeling is preferred because the label may be added at the last step of an in situ polynucleotide synthesis. Since it is standard practice to include a step in the synthesis of polynucleotides that caps unreacted chains after each base addition, labels can be appended to fill-length chains during the final synthetic cycle. Chains of less-than-fill-length ("failure sequences") are capped during previous cycles, and are therefore unable to react with the label. Full length chains can only lie in the region formed by the intersection of all of the previous synthetic steps (central region 41, 43, for example). Therefore, in accordance with the preferred embodiment, the invention not only provides information about feature location, but also unexpectedly and advantageously maps the feature sub-region that contains full-length probes and provides quality control information for each feature on the array (i.e. size of the sub-region containing full-length probe, where the larger the sub-region, the higher the quality of the data).

Once the apparatus 10 is manufactured, it is used in gene expression and mutation experiments to identify "target" nucleic acids of unknown sequences or of known sequences at unknown concentrations. The target nucleic acids are typically known to have, or suspected as having, nucleic acid sequences that are complementary to one or more of the nucleic acid probe 12 sequences immobilized on apparatus 10 as features 13. By knowing the probe 12 nucleotide sequence in the features 13, the target nucleotide sequence, if unknown, can be determined after hybridization. If the target nucleotide sequence is known, then hybridization to a properly chosen probe longer than 24 nucleotides is usually sufficient to uniquely identify the entire target. In accordance with the invention, apparatus 10 is contacted with the nucleic acid-containing target sample under conditions in which hybridization of complementary sequences can occur.

According to the present invention, hybridization is performed according to conventional methods which are well known to one skilled in the art. See for example M. Schena et al., *Science* (cited previously). Typically, apparatus 10 is overlaid with a disposable glass or plastic cover slip, after first placing a small volume of hybridization solution on top of the array. The array/cover slip assembly is placed in a constant humidity chamber, which is in turn placed in a constant temperature oven. Another hybridization apparatus is available from Affymetrix, as described in an Affymetrix product sheet for GENECHIP™ HIV PRT Assay, Part No. 700107, Rev. A, 4/96.

The array is hybridized using conventional methods and hybridization solutions. A hybridization solution that includes 6×SSPE (900 mM sodium chloride/ 60 mM sodium phosphate/ 6 mM EDTA, pH7.5), 1% w/v Triton X-100 (Amresco reagent grade, product code 0694), 100 µg/ml heat-denatured salmon sperm DNA, 1 mg/ml bovine serum albumin, 0.1% w/v sodium dodecyl sulfate and 150 µg/ml labeled target RNA or DNA is preferred. (See J. Sambrook et al., Molecular Cloning: A Laboratory Manual, cited above). The hybridization preferably occurs at 37° C. for 20 hours. The array is then washed using conventional methods. In a preferred embodiment, the protocol would be to wash at 37° C. in 0.1×SSPE containing 0.005% w/v Triton X-100 for 15 minutes. After the washing step is completed, the array is spun or blown dry, and then optically scanned to measure the degree of hybridization. Where the target is indirectly labeled, a post-hybridization stain, such as streptavidin covalently linked to a fluorophore or colloidal gold, is typically applied to the array after hybridization, but before final washing.

Features that are hybridized with target nucleic acids are illustrated by way of example in FIG. 1 as hybridized features 17 or "probe-bound hybridized targets" 17. FIG. 1 is illustrative of only one of many hybridization scenarios that may result during a hybridization assay in accordance with the invention, and FIG. 1 is not intended to limit the scope of potential assay results possible in accordance with the apparatus 10 and method 30 disclosed. As illustrated in the example shown in FIG. 1, the hybridization efficiency resulted in various targets being hybridized with probes 12 on some of the features 17 and not on other features 13. Unhybridized targets are washed away after the hybridization step.

The hybridized targets 17 are capable of producing an optical signal 18 when scanned with the light source 22 in much the same way as discussed above for the conventional array analysis. The optically detectable signal 18 from the targets indicates the occurrence of hybridization events. The optical signal 18 can be fluorescence, as described above, or can be another optical signal 18, depending on the type of label used on the target sample 17. As described above, the modified target nucleotides 17 are either labeled with a fluorophore or other label before the targets are contacted with an array substrate 11, or labeled with a fluorophore or other small organic molecule after hybridization with an array substrate 11, such that the label will associate only with probe bound hybridized targets 17. For the purposes of the invention, any method of the conventional labeling of target nucleic acids will suffice. Since the hybridization of probe features occurred at only some feature locations 17 in the example in FIG. 1, the respective optical signal 18 will be emitted at only the hybridized features 17 and not the features 13. Although not illustrated in FIG. 1, all or most probe feature may show some level of hybridization by the target sample. Therefore, the optical signals 18 from each hybridized feature location will vary from weak to strong in direct proportion to the hybridization efficiency.

Figure 2A:
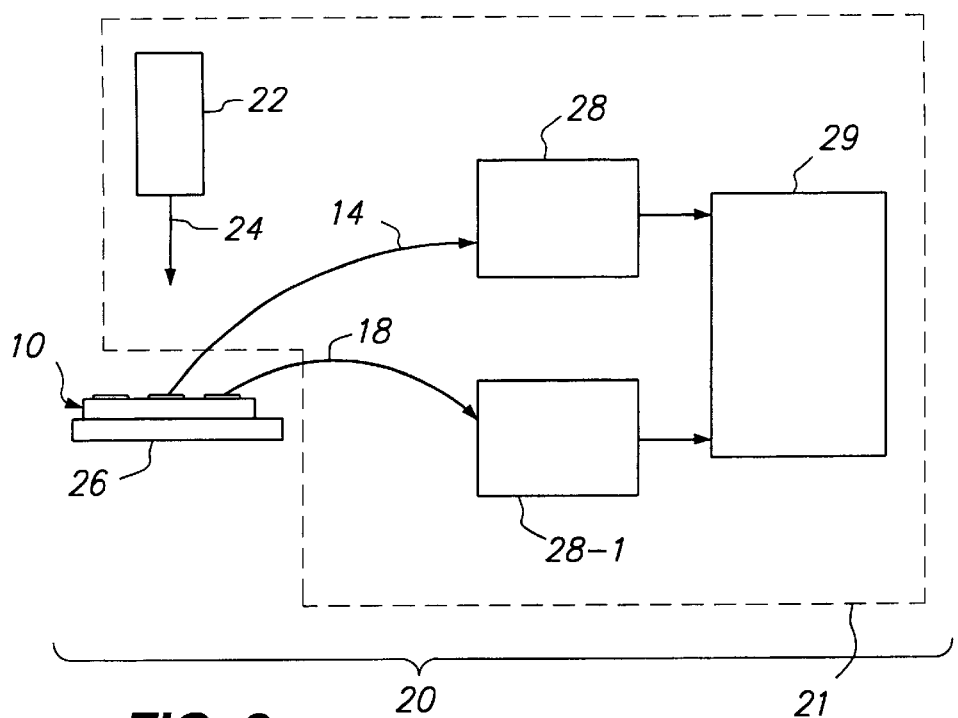
FIG. 2a illustrates the system in accordance with the present invention.

Apparatus 10, as described above, interrogated optically for feature extraction purposes with system 20 of the present invention. System 20 is illustrated in FIG. 2a and includes an optical scanning system 21 that measures the hybridized target signal 18 in a conventional fashion, and further independently measures the additional signal 14 that depends upon the presence of surface-bound or surface-containing nucleic acid probe features 13. The optical scanning system 21 comprises a light source 22, preferably a laser, which emits an excitation beam 24 onto the surface of the apparatus 10. The apparatus 10 is mounted on a stage 26. The apparatus 10 emits optical signal 14 indicative of the locations of the probe features 13 and optical signal 18 indicative of the locations of hybridized targets 17 on the surface of the substrate in respond to the excitation beam 24. A detection subsystem 28-1 for detecting the optical signal 18 from the hybridized targets 17 (usually fluorescence) is found in the conventional optical scanning system. The information gathered in the detection subsystem 28-1 is processed by the same analysis subsystem 29.

The optical system 21 extracts the probe feature signal 14 either off-axis to the original excitation beam essentially in accordance with conventional off-axis scanner technology, such as that described in U.S. Pat. No. 5,585,639, or confocally to the excitation beam with a conventional confocal scanner technology, such as that described in U.S. Pat. No. 5,760,951 (both cited above).

In the conventional confocal scanner, a reflected excitation beam is created upon excitation of an array with the light source. For the purposes of the invention, this reflected excitation beam is masked when the optical signal 14 is a scattered light signal. Since the excitation source is typically a laser, the back-reflected beam will emerge from the focusing objective lens of the present confocal scanner as a narrow, collimated beam. Scattered light will emerge over a wider solid angle; the required masking is therefore easily achieved by methods well known to the art of optical engineering. Alternatively, if the optical signal 14 is fluorescence, but distinguishable from fluorescence signal 18 from the hybridized targets 17, the confocal scanner in accordance with the invention collects the probe feature signal 14 through the fluorescence emission channel.

In all cases, the result is advantageously a parallel elaboration of functions present in the conventional scanner. For example, the additional optical signal 14 is measured during the scan, and stored in the same manner as the fluorescence signal 18 scan(s). Collection of the additional signal 14 requires the installation of optical components similar to those used to collect the hybridization signal 18, and can make use of some components (e.g. lens for confocal excitation and signal collection) already present in the scanner. An additional data channel allows the analysis of both signals 14, 18 at the analysis subsystem 29. Advantageously, implementation of the system 20 according to the present invention is cost effective, as well as providing significant improvements in the area of gene analysis.

Figure 2B:
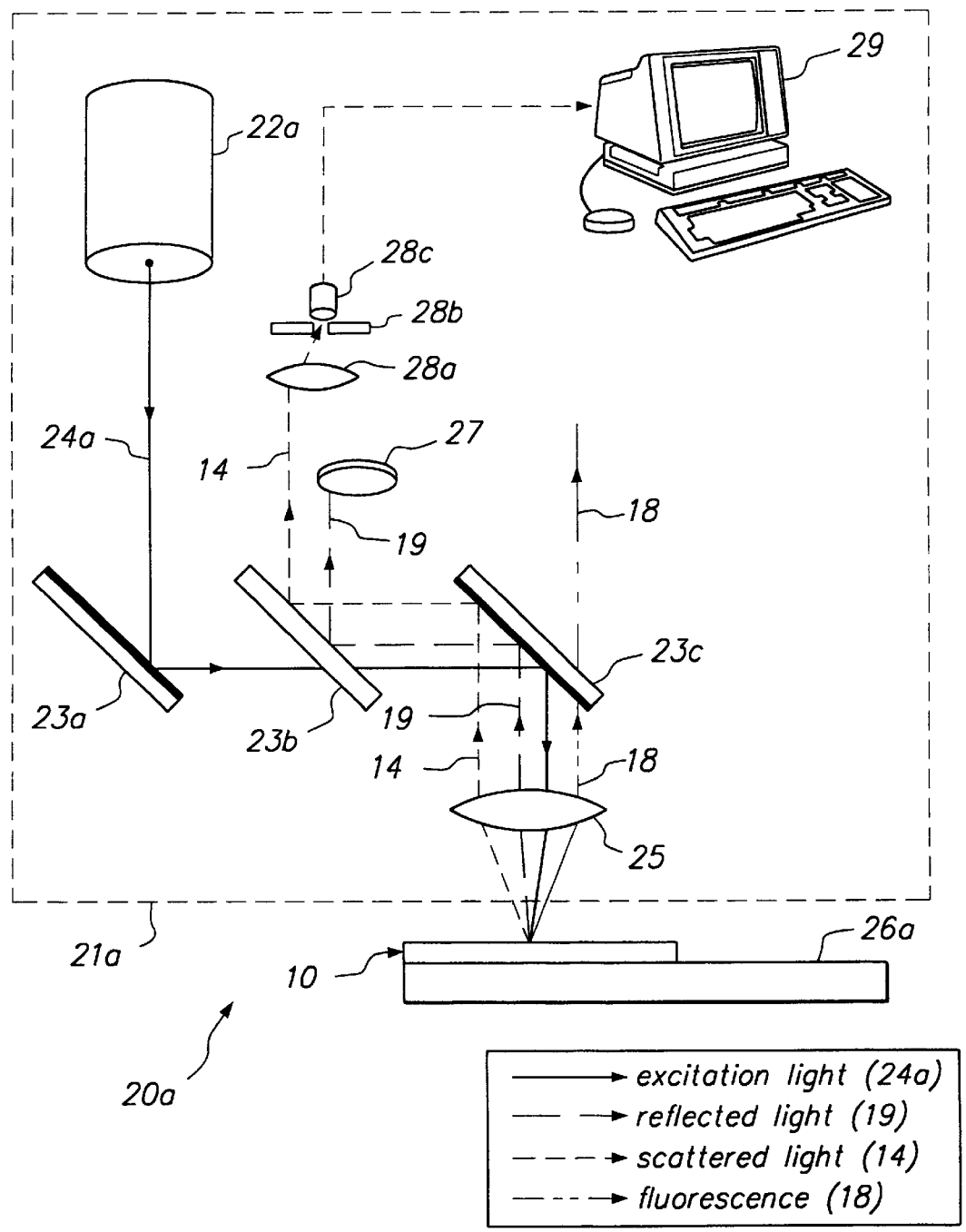
FIG. 2b illustrates the system in accordance with a preferred embodiment of the present invention.

FIG. 2b illustrates the system 20a utilizing a confocal scanning system 21a in accordance with a preferred embodiment of the present invention. A Hewlett Packard prototype confocal array scanner, using internally doubled Nd-YAG (532 nm) and HeNe (633 nm) lasers as light sources was modified for the purposes of the preferred embodiment of the present invention. Apparatus 10, which is to be interrogated, is mounted to a stage 26a of the optical scanner 21a. Excitation light 24a from a laser 22a is reflected by a mirror 23a, through a partial reflector 23b to a dichroic reflector 23c, then through an objective lens 25 onto the apparatus 10 mounted on the appropriate stage 26a. The scattered light signal 14 and back-reflected excitation light 19 are reflected by the dichroic reflector 23c, while the fluorescence signal 18 from the hybridized targets 17 on the apparatus 10 passes through the dichroic reflector 23c and hence to a conventional fluorescence detection subsystem 28-1 (not shown in FIG. 2b). Some of the scattered light 14 and back-reflected light 19 is reflected by the partial reflector 23b. The back-reflected excitation light 19 is blocked by a small beam absorber or appropriately placed iris 27. The scattered light 14 that is reflected by the partial reflector 23b is focussed by a lens 28a through a slit or pinhole 28b onto a detection device 28c. The signal 14 is then sent via an additional data channel to the same analysis subsystem 29, for example, a computer that receives the fluorescence signal(s) 18, for storage, processing and analysis. Scanning is achieved by moving the apparatus mounting stage 26a or the objective lens 25, or by inserting a beam-deflecting element, such as a galvanometer-controlled mirror (not shown), in the beam path for the excitation light 24a.

In accordance with the preferred embodiment described above, the prototype optical scanning system 21a comprises the conventional scanner components and further comprises the partial reflector 23b, beam absorber 27, and the additional detection subsystem 28, comprising the focusing optics 28a and 28b and detector 28c to uniquely detect the optical signal 14 from the probe features 13 and a data channel to provide the collected signal data to the analysis subsystem 29. It should be noted that optical scanning system 21a may also include an autofocussing device, as described in U.S. Pat. No. 5,763,870, assigned to the assignee of the present invention and incorporated herein by reference. An optical scanning system that incorporates an autofocussing device already has the optical elements needed to extract the back-reflected beam 19. Therefore, fewer modifications are needed to modify the optical scanner with autofocus in accordance with the invention to extract a probe location signal 14. A partial reflector 23b, or alternatively, a polarized beam splitter in the position of partial reflector 23b, and a quarter-wave plate (not shown) placed before objective lens 25 are already present in an optical scanner with autofocus. The reflector 23b and quarter wave plate assist in providing the back-reflected beam 19 as an input to the autofocussing device (not shown). The beam block 27 is replaced by a small reflector (not shown) that diverts the back-reflected beam 19 to the autofocussing device. Therefore, the present optical scanning system having the conventional autofocus capability essentially further comprises only the additional detection subsystem 28 comprising the focusing optics 28a and 28b and detector 28c.

If the additional optical signal 14 is fluorescence spectrally shifted from the fluorescence signal 18, then the optical scanning system 21a of the preferred embodiment requires only a filter in the path of the conventional detection optics (lens 25 and dichroic reflector 23c) and subsystem 28-1. The filter can be a monochrometer, dichroic reflector or interference filter, to sort out the fluorescence signals 14, 18.

If the additional optical signal 14 to be detected is linearly polarized light, the optical scanning system 21a of the preferred embodiment comprises a first polarizer in the input beam 24a path to provide a known beam 24a polarization at the apparatus 10 surface, and a second polarizer (90 degrees from the first polarizer) in the path of the output beam 14. Excitation light 19 reflected off the surface of apparatus 10 would have the same plane of polarization as the first polarizer and would be blocked at the second polarizer. However, the probes 12 are chiral molecules and chiral molecules rotate plane polarized light Therefore, the optical signal 14 will be rotated slightly by the chiral molecules, so that some portion of the optical signal 14 gets through the second polarizer to the second detection subsystem 28. U.S. Pat. No. 5,763,870 uses a polarizing beam splitter, which is a straightforward variation of the above-described first and second polarizers, and is well known to optical engineers.

Figure 2C:
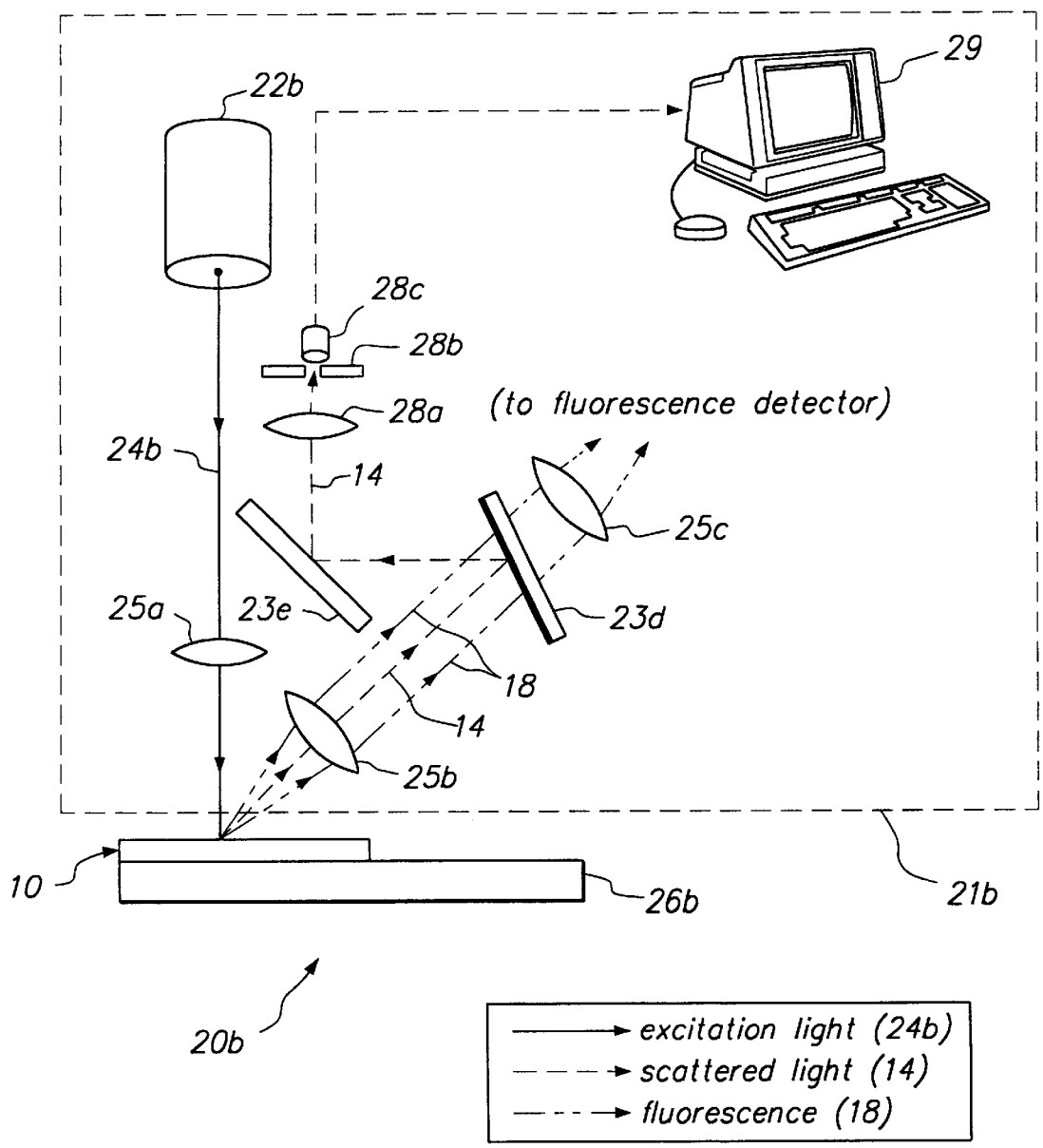
FIG. 2c illustrates the system in accordance with another preferred embodiment of the present invention.

In another embodiment, the present system 20b includes an off-axis optical scanning system 21b that detects and processes the additional optical signal 14 in accordance with the present invention. FIG. 2c illustrates system 20b using an off-axis optical scanning system 21b. Light 24b from the illumination source 22b, preferably a laser, is focussed by the objective lens 25a onto the apparatus 10 held in a holder or mounting stage 26b. Scanning is achieved by moving some combination of the objective lens 25a and holder 26b, or by inserting a beam-deflecting element, such as a galvanometer-controlled mirror, into the excitation path (not shown). The optical signal 14 from the probe feature 13 locations, in the form of scattered light, for example, and the optical signal 18 from the hybridized targets 17 locations, in the form of fluorescence, emerges off-axis and are collimated by a collection lens 25b, then split into components at the excitation and emission wavelengths by a dichroic reflector 23d. The fluorescence signal 18 passes through a second lens 25c to a fluorescence detection subsystem 28-1 (not shown in FIG. 2c). The scattered light signal 14 is steered by a mirror 23e into the scattered light detection subsystem 28 comprising detection optics 28a & 28b and detector 28c, as in the confocal scanning system 21a. The information regarding the optical signals 14 is sent by the detection subsystem 28 to the analysis subsystem 29 for storage and analysis.

Therefore, the off axis optical scanner 21b of the present invention further comprises a dichroic reflector 23d, a mirror or fill reflector 23e, and an additional detection subsystem 28, comprising focusing optics 28a and 28b and detector 28c, to separately detect the scattered light signal 14. An additional data channel connects the detection subsystem 28 to the analysis subsystem 29 provide the collected signal data to the analysis subsystem 29.

If the optical signal 14 is another fluorescence signal spectrally shifted from fluorescence signal 18 rather than the scattered light signal, then the off axis scanner 21b of the present invention would instead further comprise a filter system to filter one fluorescence signal 14 from the other signal 18 at the detection subsystem 28-1. An interference filter, monochrometer and dichroic reflector are examples of an appropriate filtering system for the invention. Moreover, if the optical signal 14 is linearly polarized light, the off axis scanner would instead further comprise a first polarizer and a second polarizer, similar to that described above for the confocal scanner 21a.

In a preferred embodiment of an off-axis scanning system 21b, a Hewlett Packard Model No. G2500A Gene Array Scanner using an Argon ion type laser light source 22b (off-axis scanner) is modified for the purposes of the invention.

In each embodiment of the system 20, the analysis subsystem 29 analyzes the detected data from the detection subsystems 28, 28-1 and the conventional system for detecting fiduciary marks (not shown), then determines the actual location of all the probe features 13. The analysis subsystem 29 further compares the actual locations of all probe features 13 with the signal 18 data collected for the hybridized targets or features 17 and provides the actual locations of the hybridized targets 17 and the identity of the nucleotide sequences in the targets 17 regardless of whether the hybridized target 17 signal 18 was weak or strong.

For the purposes of the invention, the embedded software systems used to digitize the raster scan and send it to the host computer in the analysis subsystem 29 must also be modified to process the additional data channel. Moreover, the connection to the host computer must have sufficient bandwidth to carry the additional information. Finally, the computer system and associated software must possess sufficient speed and memory capacity to properly receive and store the additional data Generally, the required modifications to the computer hardware and software of the analysis subsystem 29 again advantageously represent a parallel elaboration of functions already present in the conventional scanner system. These modifications produce improvements in computer speed and data channel bandwidth that are well within the performance specifications of currently available technology and well within the knowledge of one skilled in the computer hardware and software arts, so it will not be addressed further here.

Figure 3:
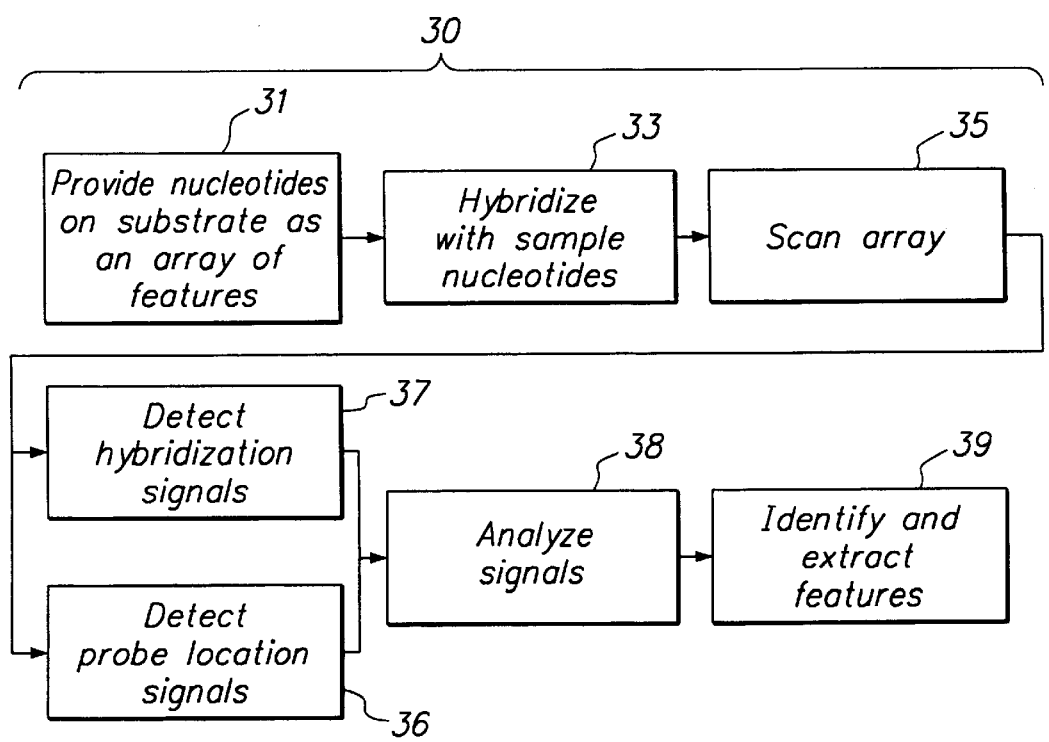
FIG. 3 illustrates a flow chart of the method in accordance with the present invention.

FIG. 3 illustrates the method 30 of the present invention. The apparatus 10 is constructed by providing (step 31) nucleotides onto a substrate as an array of discreet features via in situ synthesis or deposition. In accordance with the invention, the nucleotides have optically detectable contrast 16 from the substrate 11 regions 15 that are devoid of nucleic acids and are capable of providing a signal 14, when optically scanned. In one embodiment, the apparatus 10 is hybridized (step 33) with a sample of nucleotide targets of known or unknown sequences. The location of the hybridized targets 17 on the array is determined by optically scanning (step 35) the apparatus 10 with a light source; detecting (step 37) the hybridized target signal 18 and independently detecting (step 36) the signal 14 from the probe features 13 or probe feature contrast 16. The information gathered by the detection subsystem 28 is analyzed (step 38) by the analysis subsystem 29 to determine (step 39) the locations of the probe features 13, the locations of the hybridized targets 17, and identify the target nucleotide sequences.

An essential difference between the present apparatus 10, system 20 and method 30 and the conventional systems and methods is that the present invention does not rely on and is independent of the accuracy of the manufacturing equipment to help locate dim features. Therefore, the present apparatus 10, system 20 and method 30 overcome the problems associated with locating dim features and improve the accuracy of the feature extraction process. If the respective optical signal 18 is weak (dim feature) or the location of the hybridized target 17 is not consistent with the known locations for probe features 13 or even if the hybridized feature 17 is misshapened or improperly sized, the present invention will locate the dim feature regardless of the weak signal 18, of the location accuracy and of the dim feature's shape or size. The present apparatus 10, system 20 and method 30 do this by providing a separate independent optical signal 14 from all probe feature 13 locations and means in the optical scanning system 21 to locate all features 13, 17 in the course of the feature extraction process.

Figure 4A:
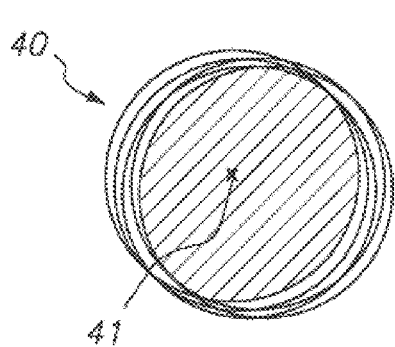
FIG. 4a and FIG. 4b illustrate two different probe deposition footprints resulting from the probe manufacturing equipment.
Figure 4B:
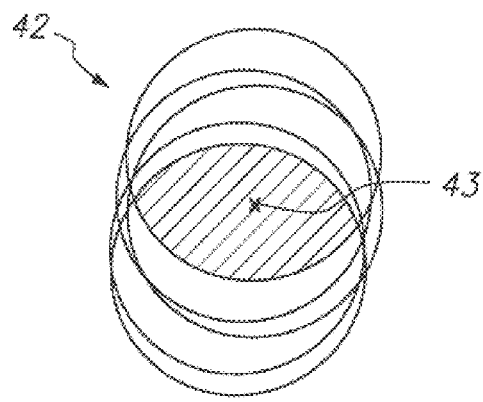
Figure 4C:
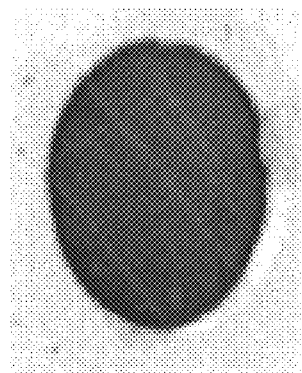
FIGS. 4c and 4d illustrate the resulting probe feature shapes from the footprints of FIGS. 4a and 4b, respectively, that are detected by the present invention.
Figure 4D:
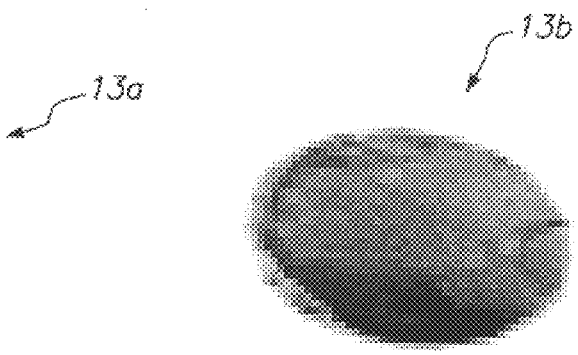

The present invention is particularly useful when the nucleic acid probes 12 are synthesized in situ, because in situ synthesis requires a separate printing step for the addition of each nucleic acid base in the probe sequence. A typical 25-base length probe fills the intersection of 25 approximately circular "footprints" of the individual printing steps. Each step introduces errors in the center locations and diameter of each footprint, such that the shape of the resulting overall feature can be quite complex, if the aiming and diameter errors are a substantial fraction of the nominal feature diameter. FIG. 4a and 4b illustrate two possible footprint scenarios 40, 42, respectively, and FIGS. 4c and 4d illustrate the feature shape that results from such footprints, respectively. While FIGS. 4a and 4c illustrate a relatively uniform footprint and feature, FIGS. 4b and 4d illustrate what happens when the centers 43 of the substantially circular footprints 42 are not placed on top of one another, as in an ideal circular feature shape. The intersection of the overlapping footprints 42 shown in FIG. 4b form an essentially football-shaped feature 13b in FIG. 4d. Effectively, there are more oligonucleotide probes on one side of the feature 13b, depending on where the expected center of the feature is predetermined to be by the manufacturing equipment.

Other more complex feature morphologies are possible from the manufacturing equipment, such as an annular shaped features and crescent shaped features. An annular feature an intensity profile that looks like a donut rather than a uniform spot. Effectively, there are more nucleic acid probes at the edges than in the center of the feature. A crescent shaped feature has an intensity profile that looks like a crescent moon with more nucleic acid probes near one edge than in the center of the feature.

Figure 4E:
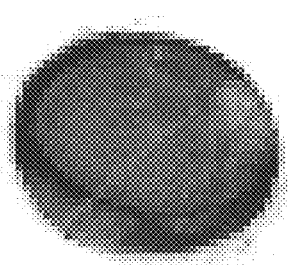
FIG. 4e illustrates a complex in situ synthesis feature morphology that is detected by the present invention.
Figure 4F:
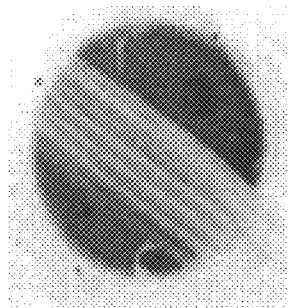
FIG. 4f illustrates a feature interrupted by surface defects in the substrate that is detected by the present invention.

FIG. 4e illustrates another complex in situ synthesis feature morphology. FIG. 4f illustrates a probe feature interrupted by a surface scratch in the substrate 11. The present invention is independent of the morphology and defects in the features. Advantageously, the present invention accurately locates probe features that have been deformed by defects in the substrate 11 surface and accurately locates all feature regardless of their shape, size and location on the substrate and regardless of the extent of hybridization (i.e. dim features).

According to the invention, the locations of the features 13, 17 are determined by exploiting the optically detectable contrast 16 between the "probe-bound substrate areas", i.e. the features 13, 17, and the "non probe-bound substrate areas", i.e. the regions 15 in FIG. 1. The optically-detectable contrast 16 may be created in many ways and, functions to produce a signal 14 when optically scanned that is detected by the detector 28 independently of the optical signal 18 produced by the hybridized targets 17. The data collected from the detected optical contrast 16 provides accurate information about the actual location of all features 13, 17. This information is correlated with the data collected from the hybridized targets 17 in the analysis subsystem 29 and the locations of, and therefore, the nucleotide sequences of, the dim and bright hybridized targets 17 alike are accurately determined.

The apparatus 10, system 20 and method 30 of the present invention assure that the distance between the center of a given feature and the center of the data extraction region is less than 10% of the nominal feature diameter. In addition, the apparatus 10, system 20 and method 30 provide data that can be used to objectively customize the shape and diameter of the extraction region, so that only pixels containing high-quality information are used to compute the average signal within a given feature. The ability to extract meaningful results from features that would otherwise need to be rejected as outlier data reduces the requirement for redundant probe features on the array, which improves the density and overall cost-effectiveness of the array. Finally, the apparatus 10, system 20 and method 30 of the present invention provide a powerful quality control tool for evaluating the overall effectiveness of in situ probe synthetic schemes.

As mentioned above, Examples 1–5 below represent some of the ways that the optical contrast 16 can be created. It is not the intent of the present invention to be limited by or to the Examples below. As long as the apparatus has optically-detectable contrast 16 between probe bound areas 13, 17 and non-probe-bound areas 15 of a substrate 11 being interrogated, and the contrast produces an optical signal 14 independently of the hybridized target signal 18 when the array is optically scanned, it is, within the scope of the present apparatus 10, system 20 and method 30.

Examples

Example 1

Probes 12 can be synthesized so that they bear a member of a specific binding pair (sbp member), e.g. a chemical tag or other small organic molecule, that is then labeled with a complementary sbp member that has a light scattering characteristic. For instance, the probes 12 might be synthesized in such a way that a biotinylated nucleotide analog is incorporated during synthesis (step 31), either in situ or prior to deposition. In the preferred embodiment of the invention, the chemical tag is added to probes 12 synthesized in situ, at the last synthetic step, and the synthetic scheme includes a capping step in each cycle of nucleotide base addition, so that the chemical tag is added only to full-length polynucleotide probes 12. The array is then labeled with a colloidal gold-streptavidin conjugate or a plastic microbead-streptavidin conjugate during or after hybridization (step 33). The streptavidin binds only to the biotin portions of the probe-containing regions 13 of the array. During array scanning (step 35), these regions 13 will scatter significantly more light off-axis to the excitation beam 22a. Detection (step 36) of this scattering light signal 14 into a separate data channel allows parallel measurement of full-length probe density (by scattering 14 at the excitation wavelength) and hybridization intensity (by fluorescence 18 at the red-shifted (longer) emission wavelength). The scattering channel can then be used during feature extraction to locate probe regions 13, independent of hybridization 17, because the features 13, 17 in the scattering channel are self-locating (i.e., they are all bright with respect to probe-free regions 15). Note that the optical signal 14, whether on-axis scatter (using optical system 21a) or off-axis scatter (using optical system 21b), is easily separated from the fluorophore fluorescence signal 18 by means of a suitable dichroic reflector (23c or 23d respectively), interference filter or monochrometer. Therefore, the presence of the label that scatters light will not degrade the fluorescence scanning performance. In a confocal scanner 21a, the scattering light optical signal 14 can also be separated from back reflected light 19, which is reflected off the surface of the substrate 11 (i.e. "noise"). The surface reflection noise or back reflected light signal 19 is separated by means of appropriate optics (25, 23c) and a simple spatial filter 27. In an off-axis scanner 21b, the signal collection geometry of the system 20b automatically prevents collection of any surface or back-reflected light (noise) 19. Note that a preferred diameter of the microbead light scattering label is $\lambda/2$ to $3\lambda/2$ for plastic beads and $\lambda/5$ to $2\lambda/5$ for colloidal gold beads, where $\lambda$ is the wavelength of the excitation light 24.

Example 1 Experiment

The feasibility of locating features 13, 17 by light scattering (optical signal 14) from bound metal colloids and fluorescence (optical signal 18) was demonstrated. In this experiment, the oligonucleotide probes 12 were not directly labeled with a light scattering agent. Instead, two samples of target nucleotide sequences were labeled with biotin to accomplish this purpose, simply due to equipment availability at the time of this experiment. The experiment also included the two target nucleotide sequences mentioned above, but instead the sequences were labeled with either fluorophores Cy3 or Cy5. The fluorescence maxima of the Cy3 and Cy5 fluorophores are spectrally distinct and distinguishable, therefore the target nucleotide sequences labeled with each fluorophore are distinguishable for the purposes of this experiment. Both the biotinylated target nucleotide sequences and the fluorophore labeled target sequences were hybridized to the complementary oligonucleotide probes in order to demonstrate the measurement of fluorescence and scattering from the same array. Streptavidin-conjugated colloidal gold particles were bound to the biotin during the hybridization step. The light scattering properties of the gold particles were enhanced for this experiment by precipitating silver onto the gold particles.

Materials

Streptavidin-labeled, 20 nm diameter colloidal gold was obtained from Sigma Chemical Company, Saint Louis, Mo. (product No. S-6514). Arrays of oligonucleotide probes having two different sequences were synthesized in situ using conventional methods by the assignee of the present invention, Hewlett-Packard, in a prototype in situ synthesis system because of its availability at the time of this experiment. Target oligonucleotides were custom synthesized by Operon Technologies, Inc., Alameda, Calif. The following target sequences were made:

The in situ synthesized oligonucleotide probe 12 sequences are not listed above, but should be readily apparent to one skilled in the art, because they are the complementary sequences to the above target sequence listings. The target sequences SEQ ID No. 1 and 2 were labeled with fluorophore labels Cy3 and Cy5, respectively, and SEQ ID No. 3 and 4 were biotinylated for the reason mentioned above. Note that the biotinylated target sequences, when hybridized to their complementary probes 12 on the array surface, place biotin in the same position as if biotin had been directly added to the probes 12 at the last synthetic step. This is because the probes 12 are synthesized 3'-to-5' and complementary oligonucleotide binding is anti-parallel (i.e. the 5'-end of one strand binds to the 3'-end of the complementary strand). A feature of the present invention is that the invention allows flexibility in the manufacture of the array apparatus 10, for example, as described above. Indirectly labeling of the probes 12 by hybridizing the probes 12 with complementary biotinylated target sequences allowed the principles of the invention to be demonstrated. What is important to the invention is that the features 13, 17 on the hybridized array 10 emit two different signals 14, 18 that can be independently detected and measured.

Bovine serum albumin (BSA) and the Silver Enhancement Kit were obtained from Sigma Chemical Company, Saint Louis, Mo. (product No's A7906 and SE-100, respectively). Herring sperm DNA was obtained from Promega, Madison, Wis. (Product No. D181B), and was denatured by heating to 95° C. for 5 minutes, then cooling rapidly, prior to use. All other reagents were obtained from Amresco, Solon, Ohio.

Procedure

The hybridization mixture was assembled by mixing the following components in the order given:

| Initial Concentration | Amount | Final Concentration |
| --- | --- | --- |
| 12 x SSPE containing 2% w/v Triton X-100 | 200.0 µl | 6 x |
| nuclease-free, sterile water | 168.0 µl | |
| 1 µM 3'biotin-HCV 21-25 (SEQ ID NO. 3) | 4.0 µl | 10 nM |
| 1 µM 3'biotin-TAR25C (SEQ ID NO. 4) | 4.0 µl | 10 nM |
| 100 nM 5'Cy3-HCV 21-25 (SEQ ID NO. 1) | 4.0 µl | 1 nM |
| 100 nM 5'Cy5-TAR25C (SEQ ID NO. 2) | 4.0 µl | 1 nM |
| 20 nm gold-streptavidin, 3.1 × 10$^{12}$ particles/ml | 16.0 µl | 1.2 × 10$^{11}$ part./ml |
| 10 mg/ml heat-denatured herring sperm DNA | 4.0 µl | 0.1 mg/ml |
| | 404.0 µl | |

Biotin was attached to the 3' ends of target oligonucleotides in order to place biotin in the same position as would be obtained by direct biotinylation of the probes at the end of in situ probe synthesis. The array was hybridized for 15 hours at 37° C. with mixing, in a hybridization apparatus, such that the hybridization mixture would efficiently mix together and be in contact with the array surface. After

```
5' Cy3-actccaccatagatcactcccctgt      (5'Cy3-HCV 21-25; SEQ ID NO.: 1)

5' Cy5-ggatacactgaccagctacgatgat     (5'Cy5-TAR25C: SEQ ID NO.: 2)

actccaccatagatcactcccctgt-3' biotin   (3'biotin-HCV 21-25; SEQ ID NO.: 3)

ggatacactgaccagctacgatgat-3' biotin   (3'biotin-TAR25C: SEQ ID NO.: 4)
``` hybridization, the apparatus was disassembled and the array was washed in 0.1×SSPE containing 0.005% w/v Triton X-100 at room temperature for 15 minutes. The array was rinsed for 10 seconds in ice-cold de-ionized, sterile water (to remove salt, which also scatters light), blown dry with filtered nitrogen gas, and stored in the dark.

Figure 5A:
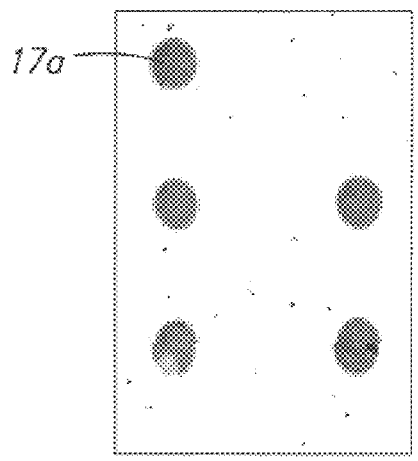
FIGS. 5a–5c illustrate assay results of an experiment using the principles of Example 1 of the present invention.
Figure 5B:
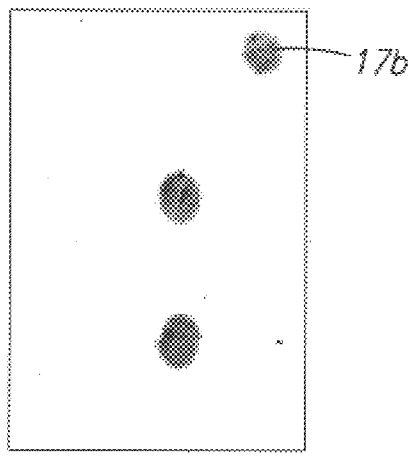
Figure 5C:
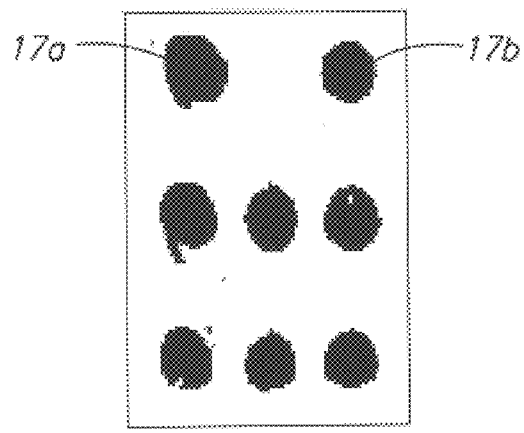

At this point, the staining of the probe regions 13 of the array by the colloidal gold was clearly visible to the naked eye. The array was scanned, using a Hewlett Packard-built laser scanner. For this experiment, the above described optical scanner 21a or 21b was not used for collection of the scattered light signal 14. Instead, for the sake of the timing of this experiment, the gold light scattering was enhanced by precipitating silver onto the gold particles, in order to increase the particle size and therefore, improve light scattering ability, to make the colloidal gold more visible to a crude scattering detector (a video camera equipped with a magnifying lens). This is another example of the flexibility provided by the present invention. The silver enhancement was performed using a commercial kit according to the manufacturer's instructions. The probe features 13 were clearly visible to the naked eye after the silver enhancement, and were photographed using the video camera Results The results of the experiment are shown in FIGS. 5a–5c. All images are shown as negatives, i.e. darker regions signify more detected light. FIG. 5a is a panel illustrating the Cy3-fluorescence image (optical signal 18a) due to binding of target 5'Cy3-HCV 21-25, SEQ ID NO.: 1 to surface bound probes 12 (hybridized targets 17a). FIG. 5b is a panel illustrating the Cy5 fluorescence image (optical signal 18b) due to binding of target 5'Cy5-TAR25C, SEQ ID NO.:2 to surface bound probes 12 (hybridized targets 17b). The binding of the two different target sequences (SEQ. ID No.: 1 and 2) occurred in the approximate locations expected from the array design specification. Note that the TAR25C, SEQ ID NO.: 2 features 17b are impossible to locate in the SEQ ID NO.: 1 Cy3 image, and the HCV 21-25, SEQ ID NO.: 1 features 17a are impossible to locate in the SEQ ID NO.: 2 Cy5 image. The reason for this is to provide a control for the sake of demonstrating the present invention. The experiment was designed to deliberately produce dim features and bright features (one of the fluorophores had dimmer fluorescence than the other), and the experiment was designed to show that the two fluorescence optical signals 18a, 18b, as well as the light scattering signal 14, are separately detected and analyzed.

The video image of silver-enhanced gold (optical signal 14) from the same region is shown in the panel in FIG. 5c. All of the features 17a, 17b are clearly visible and easily located. Thus, the information from an image like that in FIG. 5c, could be used to locate the hybridized regions to use for feature extraction of the TAR25C, SEQ ID NO.: 2 hybridized features 17b in FIG. 5b or the HCV 21-25, SEQ ID NO.: 1 hybridized features 17a in FIG. 5a.

Example 2

Substitute a 2-photon fluorophore for the chemical label in Example 1. Such labels are known to the art, and possess the unique property of emitting photons with a higher energy (blue-shifted) than the individual excitation photons of the fluorophore label on the hybridized targets 17. The 2-photon fluorophore accomplishes this feat by absorbing two photons, combining the photon energies, and emitting one photon. (See for example, C. Xu, W. Zipfel, J. B. Shear, R. M. Williams, W. W. Webb, "Multiphoton Fluorescence Excitation: New Spectral Windows For Biological Nonlinear Microscopy", *Proc. Natl. Acad. Sci USA,* 93(20) :10763-8 (October 1996)). As in Example 1, the blue-shifted location signal 14 is easily separated from the signal 18 derived from the labeled hybridized targets 17 by means of a monochrometer or appropriate interference filters.

Example 3

Nucleic acids are chiral, because nucleotides include ribose or deoxyribose sugars that can exist as different stereoisomers. Therefore, probe-containing regions 13, 17 of the surface can exhibit both birefringence and differential reflection of circularly polarized light. Either of these effects can be exploited to measure a reflected signal 14 that is dependent upon the absence or presence of surface-bound probe nucleic acids 12, which is distinguishable from the fluorescence signal 18 from the hybridized targets 17.

Example 4

Surface-bound nucleic acids 12 make the regions bearing those nucleic acids more wettable by aqueous solutions. If an array is scanned dry, it will often bear a small halo of crystallized salts at the location of each feature 13, 17. Excitation light that is scattered by these crystals can be used to locate the features, as described in Example 1.

Example 5

Substitute a profoundly red-shifted, narrow emission fluorophore for the 2-photon fluorophore in Example 2. An example of such a red-shifted fluorophore is a semiconductor nanocrystal labeling system described by M. Bruchez et al., *Science* 281, 2013–2015 (1998) incorporated herein by reference. Another example is a plastic microbead labeled with an energy-transfer fluorescent dye pair, such as Trans-FluoSpheres from Molecular Probes (Eugene, Oreg.) or labeled with rhodamine, from Sigma Chemical Co., Mo.) Once again, the feature location signal 14 is well separated spectrally from all fluorescence signals 18 from the hybridized targets 17, and can be observed independently by means of appropriate filters or a monochrometer. Example 5 experiment:

The feasibility of locating features 13, 17 by a fluorescence signal 14 emitted from surface bound probes 12, which is different from the fluorescence signal 18 from a fluorophore labeled target sequence was demonstrated. Two different probe sequences 12 were synthesized in situ, using conventional techniques, but not directly labeled for the reason mentioned above for Example I experiment. Instead, two different target nucleotide sequences were biotinylated to indirectly label the probes 12 during hybridization. Streptavidin-labeled rhodamine-containing polystyrene microspheres were bound to the biotin, thereby providing the fluorescence label to the probes 12. The rhodamine absorbs green light and fluoresces in an orange-red color. The rhodamine microspheres were used in this experiment instead of the fluorescent dye pair microspheres mentioned above for Example 5. In either case, the feasibility of using fluorescence-containing microsphere labels was demonstrated. Also, two different target nucleotide sequences were labeled with a fluorophore Cy5 that absorbs red light and fluoresce in far red spectral region. The fluorescences from the Cy5 fluorophore label and the rhodamine are spectrally distinct for the purposes of the invention, in order to demonstrate measurement of both fluorescence channels (signals 14 and 18) from the same array.

Materials

Streptavidin-labeled, 250 nm diameter rhodamine-containing polystyrene microspheres and bovine serum albumin (BSA) were obtained from Sigma Chemical Company, Saint Louis, Mo. (product No's L-6530 and A7906, respectively). Two different oligonucleotide probe sequences were synthesized in situ, as mentioned above for Example 1 experiment. One new target oligonucleotide was custom synthesized by Operon Technologies, Inc., Alameda, Calif. The following sequence was made:

5'Cy5-actccaccatagatcactcccctgt (5'Cy5 -HCV 21-25; SEQ ID NO.: 5)

The nucleotide sequences of the in situ synthesized probes 12 for the above new target sequence are not listed herein, but the probe sequences should be readily apparent to one skilled in the art due to the complementarity of the probes and targets nucleotides. The new target sequence, SEQ ID NO.: 5, was labeled with a fluorophore Cy5, like SEQ ID NO. 2. All other target nucleotide sequences, probe sequences and all other reagents used were as described in the above Example 1 experiment.

Procedure

The hybridization mixture was assembled by mixing the following components in the order given:

| Initial Concentration | Amount | Final Concentration |
|---|---|---|
| 12 x SSPE containing 2% w/v Triton X-100 | 200.0 μl | 6 x |
| 1% W/V BSA in nuclease-free, sterile water | 179.0 μl | |
| 10 mg/ml heat-denatured herring sperm DNA | 4.0 μl | 0.1 mg/ml |
| 1 μM 3'biotin-HCV 21-25 (SEQ ID NO. 3) | 4.0 μl | 10 nM |
| 1 μM 3'biotin-TAR25C (SEQ ID NO. 4) | 4.0 μl | 10 nM |
| 10 nM 5'Cy5-TAR25C (SEQ ID NO. 2) | 4.0 μl | 100 pM |
| 100 nM 5'Cy5-HCV 21-25 (SEQ ID NO. 5) | 4.0 μl | 1 nM |
| 250 nm rhodamine-streptavidin polystyrene beads | 1.0 μl | 1:400 dilution |
| | 400.0 μl | |

Biotin was attached to the 3' ends of target oligonucleotides SEQ ID NO.: 3 and 4 in order to place biotin in the same position as would be obtained by direct biotinylation of the probes 12 at the end of in situ probe synthesis. The array was hybridized for 17 hours at 37° C. with mixing, using the hybridization apparatus, as described above for the Example 1 experiment. After hybridization, the apparatus was disassembled and the array was washed in 0.1×SSPE containing 0.005% w/v Triton X-100 at room temperature for 5 minutes. The array was rinsed for 10 seconds in ice-cold de-ionized, sterile water (to remove salt, which also scatters light), blown dry with filtered nitrogen gas, and stored in the dark. The staining of the probe regions 13 of the array by the polystyrene microspheres was clearly visible to the naked eye, because the size of the microspheres was chosen to scatter light well so that (i) the spheres are visible by light scattering and (ii) the spheres are visible by the fluorescent rhodamine inside the spheres. The array was scanned, using the same Hewlett Packard-built laser scanner, as described above for Example 1 experiment and for the same reasons. However, the fluorescence signals 14, 18 were detected with a conventional fluorescence detection system 28-1, such as that described above, using a filtering device to separate the two fluorescence signals 14, 18. The fluorescences from the Cy5 and rhodamine labels were independently detected due to their above-mentioned spectral emission differences.

Results

Figure 6A:
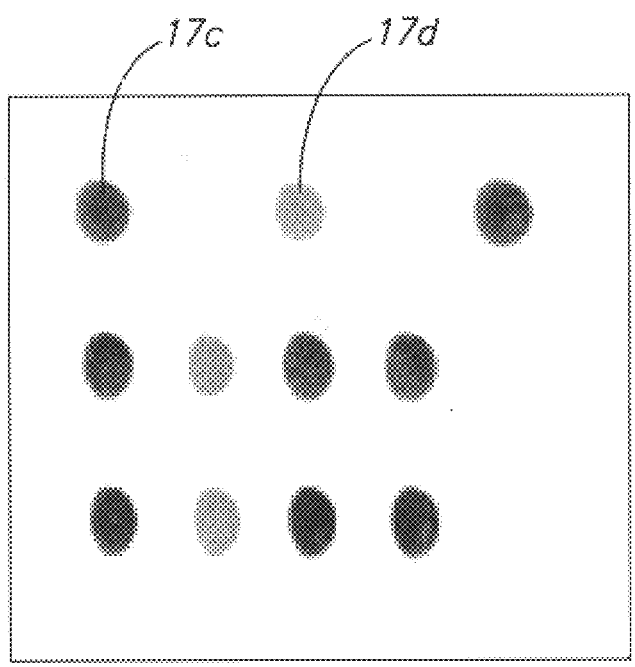
FIGS. 6a–6b illustrate assay results of an experiment using the principles of Example 5 of the present invention.
Figure 6B:
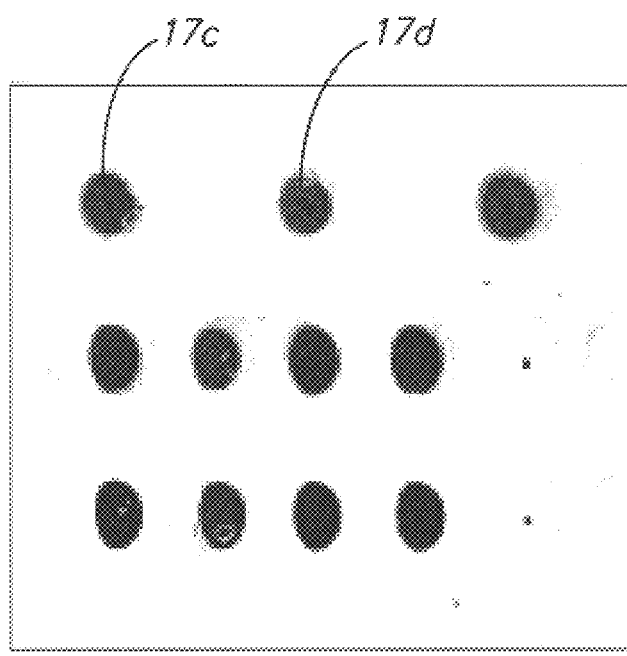

The results of the experiment are shown in FIGS. 6a and 6b. All images are shown as negatives, i.e. darker regions signify more detected light. FIG. 6a is a panel illustrating the Cy5-fluorescence image (signal 18) from the hybridized targets 5'Cy5-HCV 21-25, SEQ ID NO.: 5, to the surface bound probes 12 (hybridized targets 17c) and from the hybridized targets 5'Cy5-TAR25C, SEQ ID NO.: 2 to surface bound probes 12 (hybridized targets 17d). Note that the TAR25C, SEQ ID NO.: 2 features 17d are dimmer in the SEQ ID NO.: 5 Cy5 image, due to the lower concentration of the TAR25C, SEQ ID NO.: 2 target than of the HCV 21-25, SEQ ID NO.: 5 target. The present experiment was designed to illustrate that the present invention could detect and measure both dim and bright features 17c, 17d.

The rhodamine fluorescence image (optical signal 14), representing the location of the surface bound probes 12 in the same region, is shown in the panel in FIG. 6b. All of the features 13, 17c, 17d are clearly visible and easily located. Thus, the information from the image in FIG. 6b is used to locate the regions to use for feature extraction of the hybridized features 17c, 17d in FIG. 6a.

Any technique that causes probe-bearing regions 13 to produce an optical signal 14, or provide optically detectable contrast 16 from non-probe bearing regions 15, that is independent of the presence or absence of probe-bound (i.e., hybridized) targets 17 is capable of self-location. Such independent optical signal 14 or contrast 16 can then be used to properly locate features 17 that yield dim signals in the fluorescence (hybridization) data channel(s).

The present invention provides measurements of the real locations of nucleic acid probe features on nucleic acid probe arrays. The data can be used to significantly improve the determination of the hybridization signal from dim features. This in turn improves the detection of targets that were present at low concentration or that exhibited a low efficiency of hybridization to the probe in question. Unlike most solutions to dim feature extraction, the present invention compensates for both systematic and random errors in the manufacturing process, and is robust as probe feature size decreases.

Thus there has been described a new apparatus, systems and method for locating all features on a nucleic acid probe array, including both dim and bright hybridized features. It should be understood that the above-described embodiments are merely illustrative of the some of the many specific embodiments that represent the principles of the present invention. Clearly, numerous other arrangements can be readily devised by those skilled in the art without departing from the scope of the present invention. For example, it is within the scope of the present invention to immobilize the target sequences on the substrate into an array pattern, such that there are areas on the substrate that are devoid of target nucleic acid. The targets are capable of producing an optical signal or optical contrast when exposed to an optical stimulus. The nucleic acid probes are then hybridized to the immobilized target sequences. The probes are capable of producing a separate and distinguishable optical signal from the target signal when scanned with an optical stimulus as described above. It is the intent of the inventors to not be limited by whether the probes or the targets are immobilized on the substrate. As long as both the probes and the targets are capable of producing optical signals that are distinguishable from one another and these signals can be detected independently and analyzed to locate all nucleic acid features, it is within the scope of the invention.

What is claimed is:

1. An apparatus with self-locating nucleic acid positions in an array comprising:
   a substrate having a surface;
   a first plurality of nucleotide sequences bound to the surface of the substrate;
   regions on the substrate surface that are devoid of the first plurality of nucleotide sequences, wherein the first plurality of nucleotide sequences comprise a first optically detectable contrast from the regions; and
   a second plurality of nucleotide sequences hybridized to complementary nucleotide sequences of the first plurality of nucleotide sequences, the second plurality of nucleotide sequences comprising a second optically detectable contrast distinguishable from the first optically detectable contrast,
   wherein the first optically detectable contrast comprises a first optical signal and the second optically detectable contrast comprises a second optical signal when scanned with an optical scanner, the first optical signal being independent of the second optical signal, such that the first optical signal indicates the location of the first plurality of nucleotide sequences in the array independently of the hybridization by the second plurality of nucleotide sequences.

2. The apparatus of claim 1, wherein the first plurality of nucleotide sequences comprises a plurality of oligonucleotide probes and the second plurality of nucleotide sequences comprises a plurality of target nucleotide sequences.

3. The apparatus of claim 1, wherein the first plurality of nucleotide sequences comprises a first signal producing system to produce the first optical signal, and wherein the second plurality of nucleotide sequences comprises a second signal producing system to produce the second optical signal.

4. The apparatus of claim 3, wherein the first signal producing system comprises a first label and the second signal producing system comprises a second label.

5. The apparatus of claim 4, wherein the first label comprises a specific binding pair comprising biotin and colloidal gold chemically conjugated to streptavidin, and wherein the first optical signal comprises scattered light.

6. The apparatus of claim 4, wherein the first label comprises a first fluorophore and wherein the first optical signal comprises a spectrally shifted fluorescence produced by the first fluorophore relative to the second optical signal.

7. The apparatus of claim 4, wherein the first label comprises a specific binding pair comprising biotin and plastic microspheres chemically conjugated to streptavidin, the microspheres containing a fluorescent material, and wherein the first optical signal comprises fluorescence spectrally shifted from the second optical signal.

8. The apparatus of claim 1, wherein the first plurality of nucleotide sequences are surrounded by dried crystallized salts on the substrate, and wherein the first optical signal comprises scattered light from the crystallized salts.

9. The apparatus of claim 1, wherein the first plurality of nucleotide sequences reflects light along a plan e of polarization, and wherein the first optical signal comprises a reflected signal in which the plane of polarization of the reflected light has been rotated by interaction with chiral portions of the first plurality of nucleotide sequences.

10. The apparatus of claim 1, wherein the second plurality of nucleotide sequences comprises a fluorophore label, and wherein the second optical signal comprises fluorescence produced by the fluorophore.

11. A system for locating nucleic acid positions in an array comprising:
 a substrate having a surface;
 a first plurality of nucleotide sequences bound to the surface of the substrate;
 regions on the substrate surface that are devoid of the first plurality of nucleotide sequences, wherein the first plurality of nucleotide sequences comprise a first optically detectable contrast from the regions;
 a second plurality of nucleotide sequences hybridized to at least some sequences of the first plurality of nucleotide sequences, the second plurality of nucleotide sequences comprising a second optically detectable contrast distinguishable from the first optically detectable contrast; and
 an optical system for optically scanning the surface of the substrate, such that the first optically detectable contrast comprises a first optical signal and the second optically detectable contrast comprises a second optical signal independently of the first optical signal, for detecting the first optical signal independently of the second optical signal, for analyzing the first optical signal to locate the first plurality of nucleotide sequences, and independently for analyzing the second optical signal for hybridization by the second plurality of nucleotide sequences on the substrate.

12. The system of claim 11, wherein the first plurality of nucleotide sequences comprises a plurality of oligonucleotide probes and the second plurality of nucleotide sequences comprises a plurality of target nucleotide sequences.

13. The system of claim 11, wherein the first plurality of nucleotide sequences comprises a first signal producing system to produce the first optical signal, and wherein the second plurality of nucleotide sequences comprises a second signal producing system to produce the second optical signal.

14. The system of claim 11, wherein the first plurality of nucleotide sequences are surrounded by dried crystallized salts on the substrate, and wherein the first optical signal comprises scattered light from the dried crystallized salts.

15. The system of claim 11, wherein the first plurality of nucleotide sequences reflects light along a plane of polarization, and wherein the first optical signal comprises a reflected signal in which the plane of polarization of the reflected light has been rotated by interaction with chiral portions of the first plurality of nucleotide sequences.

16. The system of claim 11, wherein the second plurality of nucleotide sequences comprises a fluorophore label, and wherein the second optical signal comprises fluorescence.

17. The system of claim 11, wherein the optical scanning system comprises
 a first detection subsystem for detecting the first optical signal having a first input and a first output;
 a second detection subsystem for detecting the second optical signal independently of the first detection subsystem and having a second input and a second output; and
 an analysis subsystem having inputs and outputs, wherein the first output from the first detection subsystem and second output from the second detection subsystem are received by the inputs of the analysis subsystem, and wherein the outputs of the analysis subsystem comprise the location of the first plurality of nucleotide sequences and the location of the second plurality of nucleotide sequences on the substrate.

18. The system of claim 17, wherein the optical scanning system further comprises a signal filtering device and a full reflector, the signal filtering device comprising one or more of a dichroic reflector, an interference filter and a monochrometer, wherein the signal filtering device filters the first optical signal from the second optical signal and the full reflector directs the first optical signal into the first detection subsystem.

19. The system of claim 17, wherein the optical scanning system further comprises a partial reflecting device for reflecting the first optical signal into the first detection subsystem and for reflecting signal noise absorbing device.

20. A method for locating nucleic acid positions on a substrate comprising the steps of:
 providing a first plurality of nucleotide sequences on a substrate surface in a pattern such that there are regions on the substrate surface that are devoid of the first plurality of nucleotide sequences, the first plurality of nucleotide sequences comprising a first optically detectable contrast from the regions;
 hybridizing at least some of the first plurality of nucleotide sequences with a second plurality of nucleotide sequences, the second plurality of nucleotide sequences comprising a second optically detectable contrast distinguishable from the first optically detectable contrast;
 optically scanning the substrate surface such that the first optically detectable contrast comprises a first optical signal and the second optically detectable contrast comprises a second optical signal;
 independently detecting the first optical signal and the second optical signal; and
 determining the locations of the first plurality of nucleotide sequences and the second plurality of nucleotide sequences on the substrate based on the detected first optical signal and the detected second optical signal.

21. The method of claim 20, wherein the first plurality of nucleotide sequences comprises a plurality of oligonucleotide probes and the second plurality of nucleotide sequences comprises a plurality of target nucleotide sequences.

22. The method of claim 20, wherein the step of providing comprises the step of incorporating a first signal producing system on the first plurality of nucleotide sequences, and wherein the step of hybridizing comprises the step of incorporating a second signal producing system on the second plurality of nucleotide sequences.

23. The method of claim 22, wherein the step of incorporating a first signal producing system comprises the step of labeling the first plurality of nucleotide sequences with a first label, and wherein the step of incorporating a second signal producing system comprises the step of labeling the second plurality of nucleotide sequences with a second label.

24. The method of claim 23, wherein the step of labeling comprises labeling the first plurality of nucleotide sequences with a first fluorophore, the step of hybridizing comprises the step of labeling the second plurality of nucleotide sequences with a second fluorophore, the first fluorophore having a first fluorophore having first fluorescence that is spectrally shifted from a second fluorescence from the second fluorophore, and wherein the step of detecting comprises detecting the second fluorescence as the second optical signal and detecting the spectrally shifted first fluorescence as the first optical signal.

25. The method of claim 20, wherein the step of providing comprises the step of incorporating a first member of a specific binding pair on the first plurality of nucleotide sequences, and before the optical scanning step, the method further comprises the step of adding a second member of the specific binding pair to the first member, the step of hybridizing comprises the step of labeling the second plurality of nucleotide sequences with a fluorophore, and wherein the step of independently detecting comprises detecting fluorescence as the second optical signal and independently detecting the first optical signal from the specific binding pair.

26. The method of claim 20, wherein the step of hybridizing comprises the step of labeling the second plurality of nucleotide sequences with a fluorophore, and wherein the method further comprises, after the step of hybridizing, the step of drying the substrate such that crystallized salts surround the plurality of nucleotide sequences, and wherein the step of detecting comprises detecting a scattered light first optical signal from the crystallized salts and a fluorescence second optical signal from the second plurality of nucleotide sequences.

27. The method of claim 20, wherein the first plurality of nucleotide sequences reflects light along a plane of polarization, and wherein the step of detecting comprises detecting the first optical signal comprising a reflected signal in which the plane of polarization of the reflected light has been rotated by interaction with chiral portions of the first plurality of nucleotide sequences bound to the substrate surface.

28. The method of claim 20, wherein the step of hybridizing comprises the step of labeling the second plurality of nucleotide sequences with a fluorophore and the second optical signal comprises fluorescence produced by the fluorophore.

29. The method of claim 20, wherein the step providing comprises the step of synthesizing a plurality of full-length polynucleotide sequences in situ on the substrate for each of the first plurality of nucleotide sequences, wherein the step of synthesizing comprises steps of:
a plurality of sequential steps of adding a nucleotide to a single end of each polynucleotide sequence; and
after the last step of adding, the step of labeling a last nucleotide of the full-length polynucleotide sequences with a member of a signal producing system.

30. The method of claim 29, wherein the step of labeling comprises the step of adding a label as the member of the signal producing system to the last nucleotide of the full-length polynucleotide sequences and wherein the step of determining comprises further determining what percentage of the first plurality of nucleotide sequences contains the full-length polynucleotide sequences from the first optical signal produced by the member.

31. The method of claim 30, wherein the step of adding a label comprises adding a member of a specific binding pair to the last nucleotide of the full-length polynucleotide sequences.

32. The method of claim 31, wherein the step of hybridizing comprises the step of adding a complementary member to the member of the specific binding pair on the last nucleotide of the full-length polynucleotide sequences.

33. The method of claim 31, further comprising, after the step of hybridizing, the step of adding a complementary member to the member of the specific binding pair on the last nucleotide of the full-length polynucleotide sequences.

34. The method of claim 20, wherein the steps of determining comprises the step of identifying the locations of the first plurality of nucleotide sequences regardless of the extent of hybridization by the second plurality of nucleotide sequences.

* * * * *